United States Patent [19]

Foster et al.

[11] Patent Number: 5,708,997
[45] Date of Patent: Jan. 20, 1998

[54] HOSPITAL BED

[75] Inventors: L. Dale Foster; Ryan Anthony Reeder, both of Brookville; John David Vogel, Columbus, all of Ind.

[73] Assignee: Hill-Rom Company, Inc., Batesville, Ind.

[21] Appl. No.: 755,480

[22] Filed: Nov. 22, 1996

Related U.S. Application Data

[60] Division of Ser. No. 277,243, Jul. 19, 1994, Pat. No. 5,577,279, which is a continuation-in-part of Ser. No. 234,403, Apr. 28, 1994, Pat. No. 5,454,126, which is a continuation-in-part of Ser. No. 186,657, Jan. 25, 1994, Pat. No. 5,479,666, and a continuation-in-part of Ser. No. 230,061, Apr. 21, 1994, Pat. No. 5,513,406, which is a continuation-in-part of Ser. No. 186,657, and a continuation-in-part of Ser. No. 221,748, Mar. 31, 1994, and a continuation-in-part of Ser. No. 221,633, Apr. 1, 1994, Pat. No. 5,483,709, and a continuation-in-part of Ser. No. 7,122, Jan. 21, 1993, Pat. No. 5,337,845, which is a continuation-in-part of Ser. No. 912,826, Jul. 13, 1992, Pat. No. 5,335,651, which is a continuation-in-part of Ser. No. 874,586, Apr. 24, 1992, Pat. No. 5,370,111, which is a continuation-in-part of Ser. No. 524,038, May 16, 1990, Pat. No. 5,117,521.

[51] Int. Cl.$^6$ ..................................................... A61G 7/015
[52] U.S. Cl. .............................. 5/618; 5/624; 5/613
[58] Field of Search ............................. 5/602, 613, 617, 5/618, 624

[56] References Cited

U.S. PATENT DOCUMENTS

| | | | |
|---|---|---|---|
| 3,220,021 | 11/1965 | Nelson | 5/618 |
| 3,220,022 | 11/1965 | Nelson | 5/618 |
| 3,406,772 | 10/1968 | Ahrent et al. | |
| 3,898,702 | 8/1975 | Goodman | 5/618 |
| 4,258,445 | 3/1981 | Zur | |
| 4,862,529 | 9/1989 | Peck | |
| 5,454,126 | 10/1995 | Foster et al. | 5/624 X |
| 5,479,666 | 1/1996 | Foster et al. | 5/618 X |
| 5,537,701 | 7/1996 | Elliott | 5/617 |
| 5,577,279 | 11/1996 | Foster et al. | 5/618 |

*Primary Examiner*—Michael F. Trettel
*Attorney, Agent, or Firm*—Barnes & Thornburg

[57] ABSTRACT

A hospital bed has a base with casters, a main frame mounted above the base, a patient support platform movably mounted on the main frame including a leg panel, and a toilet module disposed beneath the patient support platform and normally concealed by the leg panel. The platform moves toward a head end of the bed retracting the leg panel from over the toilet module exposing the toilet module for use. The leg panel pivots downwardly after exposing the toilet module, and a head panel pivots upwardly to configure the hospital bed into a chair position. Bolsters are located outboard of each lateral edge of the leg panel and provide side support to a patient moving from the platform to the toilet module and back. A pair of pivoting footboard halves or foot gates are operably mounted to the platform and retract with the platform to between the foot and head end casters. Downward forces applied to the foot gates when utilized as hand rails are applied intermediate the foot and head end casters. A frame is mounted to the bed and a travelling harness is mounted to the frame and is adapted to be secured to a patient to provide security and stability as the patient egresses from the bed and moves onto the toilet module.

13 Claims, 13 Drawing Sheets

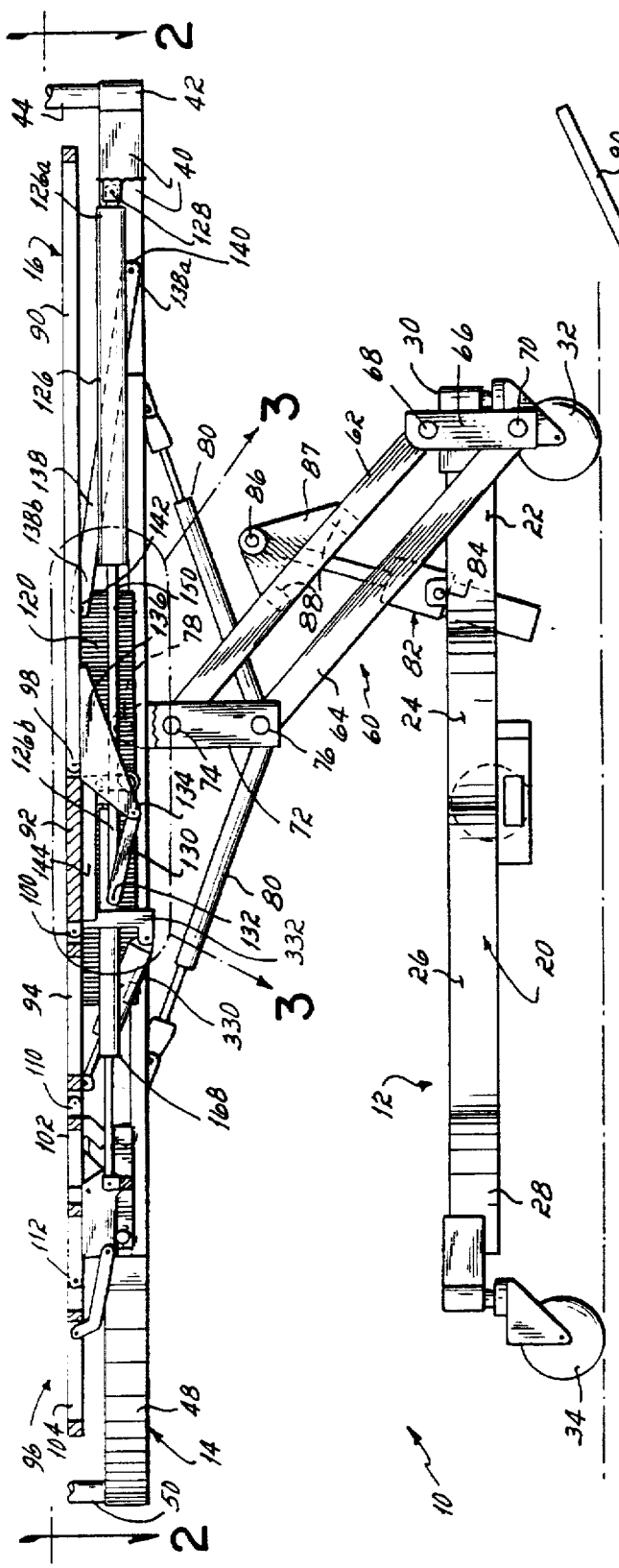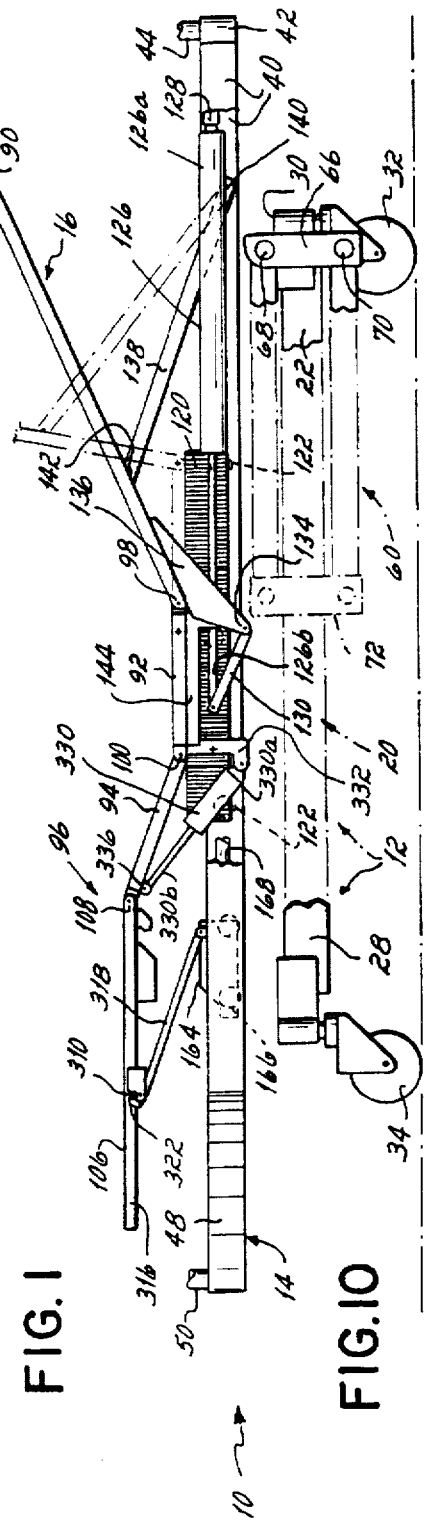
FIG.1
FIG.10

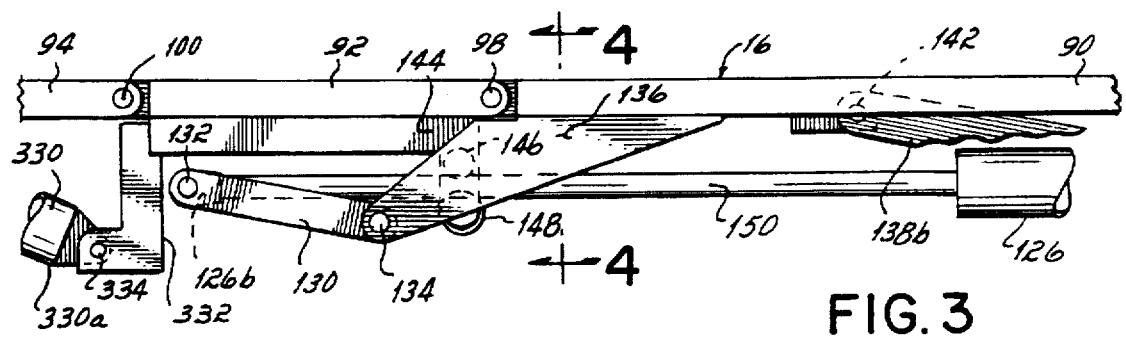
FIG. 3
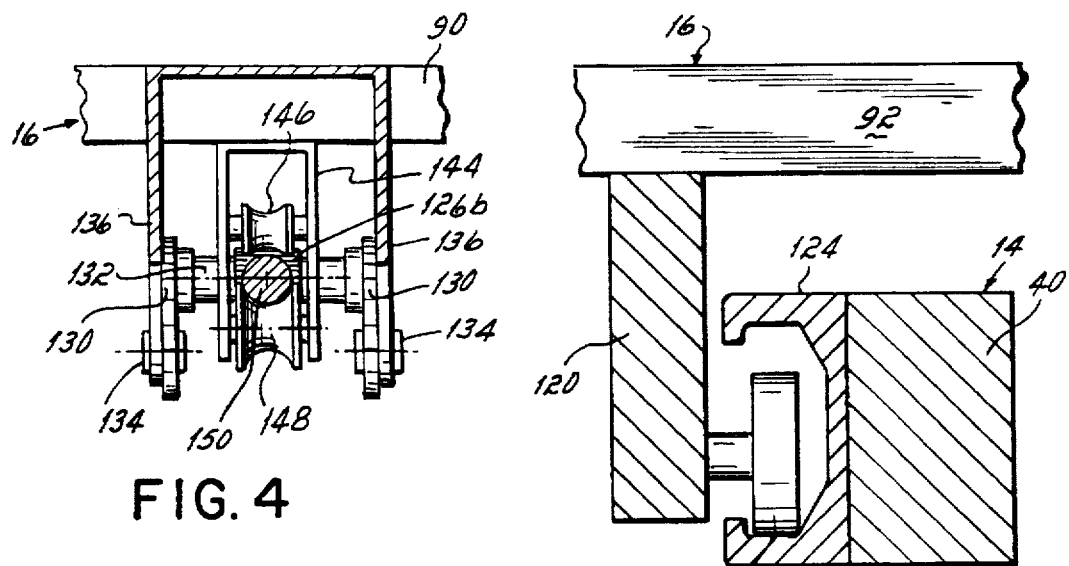
FIG. 4
FIG. 6
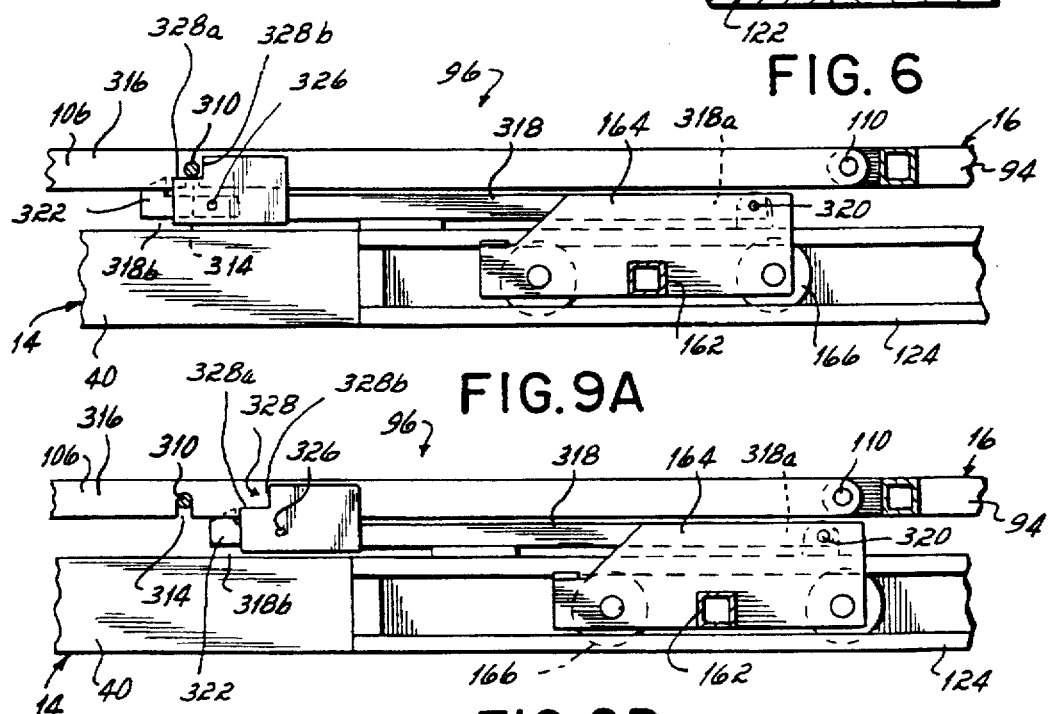
FIG. 9A
FIG. 9B

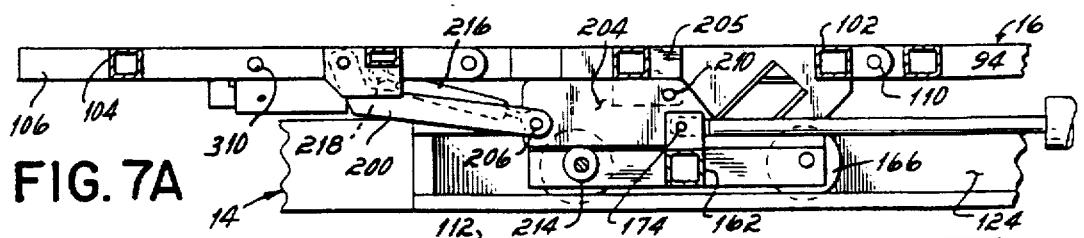
FIG. 7A
FIG. 7B
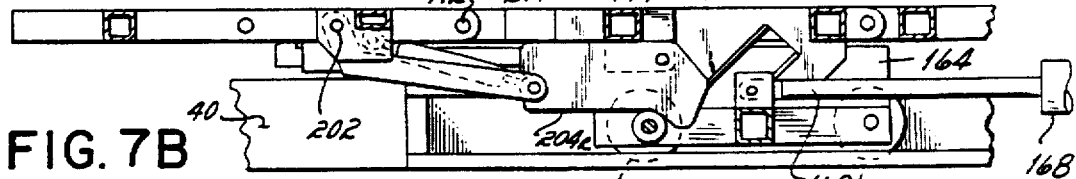
FIG. 7C
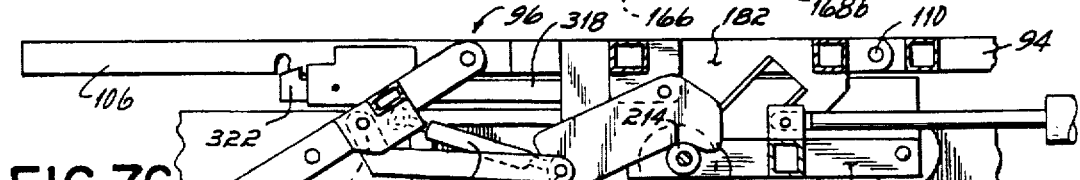
FIG. 7D
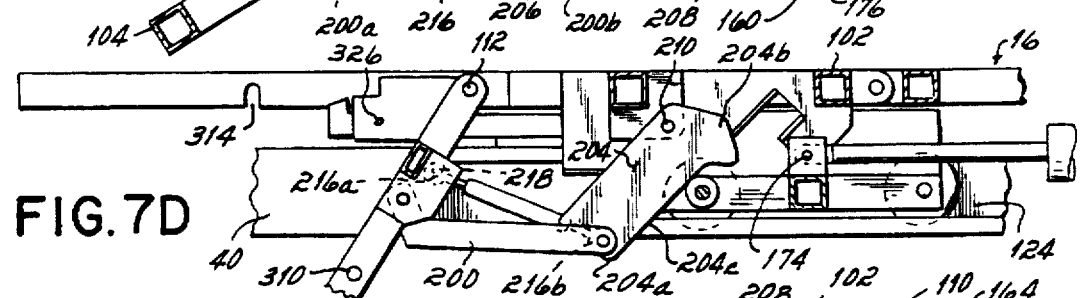
FIG. 7E
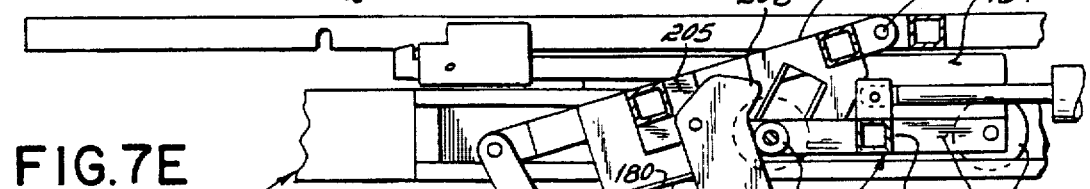
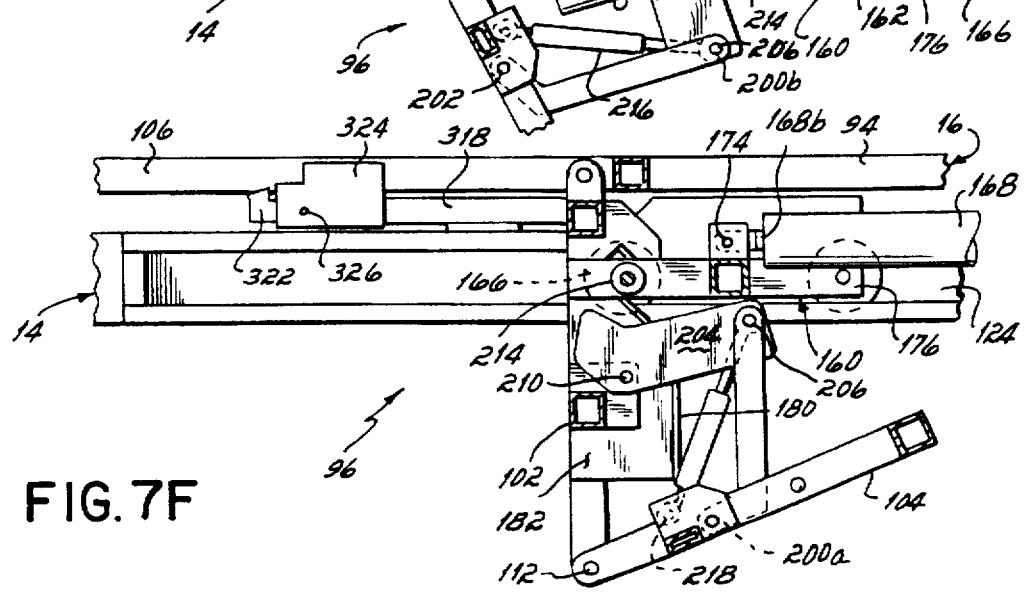
FIG. 7F

HOSPITAL BED

RELATED APPLICATIONS

This application is a divisional of application Ser. No. 08/277,243, filed Jul. 19, 1994, now U.S. Pat. No. 3,577,279 which is a continuation in part of application Ser. No. 08/234,403, filed Apr. 28, 1994, entitled FOOT EGRESS CHAIR BED, now U.S. Pat. No. 5,454,126, which is a continuation in part of application Ser. No. 08/186,657, filed Jan. 25, 1994, entitled FOOT EGRESS CHAIR BED, now U.S. Pat. No. 5,779,666, and a continuation in part of application Ser. No. 08/230,061, filed Apr. 21, 1994, entitled MODULAR HOSPITAL BED AND METHOD OF PATIENT HANDLING, now U.S. Pat. No. 5,513,406, which is a continuation in part of application Ser. No. 08/186,657, filed Jan. 25, 1994, now U.S. Pat. No. 5,479,666, entitled FOOT EGRESS CHAIR BED, a continuation in part of application Ser. No. 08/221,748, filed Mar. 31, 1994, entitled PATIENT WEIGH SCALE, still pending a continuation in part of application Ser. No. 08/221,633, filed Apr. 1, 1994, entitled LOW AIR LOSS MATTRESS WITH RIGID INTERNAL BLADDER AND AIR PALLET, now U.S. Pat. No. 5,983,709, and a continuation in part of application Ser. No. 08/007,122, filed Jan. 21, 1993, entitled VENTILATOR, CARE CART AND MOTORIZED TRANSPORT EACH CAPABLE OF NESTING WITHIN AND DOCKING WITH A HOSPITAL BED BASE, now U.S. Pat. No. 5,337,845 which is a continuation in part of application Ser. No. 07/912,826, filed Jul. 13, 1992, entitled VENTILATOR AND CARE CART EACH CAPABLE OF NESTING WITHIN AND DOCKING WITH A HOSPITAL BED BASE, now U.S. Pat. No. 5,335,651, which is a continuation in part of application Ser. No. 07/874,586, filed Apr. 24, 1992, entitled MOBILE VENTILATOR CAPABLE OF NESTING WITHIN AND DOCKING WITH A HOSPITAL BED BASE, now U.S. Pat. No. 5,370,111 which is a continuation in part of application Ser. No. 07/524,038, filed May 16, 1990, now U.S. Pat. No. 5,117,521, entitled CARE CART AND TRANSPORT SYSTEM, all of which are hereby incorporated by reference herein as if fully set forth in their entirety.

FIELD OF THE INVENTION

This invention relates generally to hospital beds, and more particularly to hospital beds which convert from a bed configuration to a chair configuration and which, in doing so, provide for patient egress from the foot end of the bed and access to an onboard patient care module.

BACKGROUND OF THE INVENTION

During a patient's stay in a hospital, the patient is normally confined to his or her hospital bed for some period of time, at least initially. During this portion of the patient's hospital stay, all of the care functions provided by attending physicians, nurses and the like are provided to the patient as he or she resides on the hospital bed.

Since the patient is not ambulatory during this period of his or her stay, the patient is unable to leave the hospital bed and travel to, for example, the bathroom. Thus, attending personnel must provide the patient with a bedpan for use on the bed. As is appreciated, use of a bedpan on a hospital bed by a patient who is in a generally supine position is difficult and cumbersome, at best.

It has therefore been an objective of the present invention to provide a hospital bed which includes an on-board toilet module which permits use by a patient in a conventional manner as opposed to the difficulties encountered with use of a traditional bedpan.

Hospital beds which convert to a chair configuration have been known for some time. Particular types of chair beds which provide for convenient and ready egress of a patient from the foot end of the bed when the bed is configured into a chair configuration are disclosed in co-pending applications Ser. Nos. 08/234,403 and 08/186,657 assigned to the assignee of the present invention. In those applications, chair beds are disclosed which have vacatable foot sections which, when the patient support platform is lowered to a lowermost position, allow the patient's feet to rest directly on the floor. Sideguards/handrails are provided on the foot end of the bed and are convertible from pivoting footboard halves for grasping by a patient to aid in egressing from the chair configured bed and in moving from a sitting position to a standing position. The patient can manipulate the vertical control of the hospital bed to assist the patient in moving from a stooped position to an upright position.

Another objective of the present invention has been to provide a hospital bed which provides for repositioning sideguards/handrails which are located at the foot end of the bed to a position intermediate the foot end and head end casters such that any downward load applied by a patient to the sideguards/handrails is applied intermediate the head and foot end casters in order to optimize the stability of the bed as a patient egresses from the bed and moves from a sitting position to a standing position.

In a chair bed of the type as disclosed in co-pending applications Ser. Nos. 08/234,403 and 08/186,657, the patient may have occasion to move from the chair configured bed to a patient care module positioned at the foot end of the bed, such as, for example, an exerciser, a scooter or walker, a toilet or a wheelchair, as disclosed in co-pending application Ser. No. 08/230,061 also assigned to the assignee of the present invention. It would be helpful if structure were provided to help guide and stabilize the patient as the patient moves from the chair configured bed to the patient care module.

It has therefore been yet another objective of the present invention to provide apparatus for stabilizing and guiding a patient from a chair configured hospital bed to a patient care module positioned at the foot end of the hospital bed.

SUMMARY OF THE INVENTION

The present invention attains the stated objectives by providing, in a preferred embodiment, a hospital bed comprising a base with casters, a main frame mounted above the base, a patient support platform longitudinally movably mounted on the main frame and including a leg panel, and a toilet module disposed beneath the patient support platform and normally concealed by the leg panel. The patient support platform and toilet module are configured such that when the patient support platform is moved toward a head end of the bed the leg panel retracts from over the toilet module exposing the toilet module for use by a patient. The leg panel pivots downwardly after retracting from over the toilet module, and the patient support platform further includes an upwardly pivoting head panel, the bed being configured such that when the leg panel is pivoted downwardly the head panel is pivoted upwardly, the bed assumes a chair position.

The patient support platform further includes a pair of bolsters, one of which is located outboard of each lateral edge of the leg panel. The leg panel and bolsters are configured such that after the leg panel has been pivoted downwardly the bolsters provide side support to a patient moving from the patient support platform to the toilet module and back.

The main frame of the hospital bed of the present invention includes a pair of spaced, longitudinal, generally parallel rails, with each of the rails having a foot end which diverges laterally outwardly. The laterally outwardly divergent foot ends of the main frame rails provide structure for guidingly docking therebetween a rollable patient care module, for example toilet, wheelchair or the like, to the main frame.

According to another aspect of the present invention, a hospital bed is provided which comprises a base having head and foot ends and casters mounted on the head and foot ends, a main frame mounted above the base, a patient support platform longitudinally movably mounted on the main frame, and a pair of pivoting footboard halves operably mounted to the patient support platform one of which is located on each lateral side at a foot end thereof. The footboard halves when oriented laterally to the bed function together as a footboard and when oriented longitudinally to the bed function separately as sideguards/handrails. The base and footboard halves are configured such that when the patient support platform is moved toward a head end of the bed the footboard halves are retracted to between the foot end casters and the head end casters. The patient support platform includes a downwardly pivoting leg panel and an upwardly pivoting head panel. The bed is configured such that when the patient support platform is moved toward the head end of the bed, the leg panel is pivoted downwardly and the head panel is pivoted upwardly, such that the bed assumes a chair position. A patient egressing from the chair configured bed and moving from a sitting position to a standing position while utilizing the sideguards/handrails applies a downward force via the sideguards/handrails intermediate the foot end casters and the head end casters, thus providing for maximum stability.

According to yet another aspect of the present invention, a hospital bed comprises a base with casters, a main frame mounted above the base, and a patient support platform mounted on the main frame and including a seat panel, a downwardly pivoting leg panel and an upwardly pivoting head panel, and a pair of bolsters one of which is located outboard of each lateral edge of the leg panel. The bolsters are movable from a position forward of and in a plane defined by the seat panel to a position above and along each lateral edge of the seat panel when the leg panel is pivoted downwardly and the head panel is pivoted upwardly to provide arm rests for a patient situated atop the bed configured as a chair.

According to yet a further aspect of the present invention, a hospital bed comprises a base with casters, a main frame having head and foot ends mounted above the base, a patient support platform having head and foot ends longitudinally movably mounted on the main frame and including a downwardly pivoting leg panel and an upwardly pivoting head panel. The patient support platform is configured such that when the patient support platform is moved toward a head end of the main frame the leg panel pivots downwardly and the head panel pivots upwardly, the bed thereby assuming a chair position. A frame is mounted to the head of the main frame and the foot end of the main frame and extends along and over the patient support platform. A traveling harness is mounted to the frame and is adapted to be secured to a patient. The traveling harness provides security and stability to a patient as the patient egresses from the bed configured as a chair and moves from a sitting position to a standing position and onto a patient care module positioned at the foot end of the main frame.

According to still a further aspect of the present invention, the frame mentioned above is mounted to the head end of the main frame and is operably mounted to the foot end of the patient support platform. The frame is operable to extend and retract along the length thereof as the patient support platform extends and retracts on the main frame. The frame is an orthopedic frame which maintains a relative distance between the frame and a patient on the patient support platform as the platform extends and retracts.

In order to carry out the longitudinal movement of the patient support platform and the pivotal movement of the leg panel, the present invention provides a first piston and cylinder drive for moving the patient support platform longitudinally toward the head end of the bed, and a second piston and cylinder drive for pivoting the leg panel downwardly after the patient support platform has traveled a predetermined distance toward the head end of the main frame in order to first clear the onboard patient care module. The leg panel comprises a calf panel pivoted relative to the main frame and a foot panel pivoted to the calf panel. A first linkage is operable between the foot and calf panels for pivoting the foot panel relative to the calf panel, and a second linkage is operable between the calf panel and the main frame for pivoting the calf panel relative to the main frame, with both the linkages being actuated by the second piston and cylinder drive.

The first linkage comprises a first link having first and second ends, the first end being pivoted to the foot panel, a second link having first and second ends, the first end being pivoted to the second end of the second link, the second end having a protuberance thereon, the second link being pivoted to the calf panel intermediate the first and second ends, and a roller operably connected to the first piston and cylinder drive and normally contacting the second link intermediate the first and second ends. When the first piston and cylinder drive is actuated the roller rides along the second link towards the protuberance; the second link rotates in response thereto causing a force to be applied to the first link which moves the foot panel downwardly relative to the calf panel. The first linkage further includes a spring operable between the foot panel and the first end of the second link.

The second linkage comprises at least a second roller operably connected to the first drive, the calf panel including a roller bearing plate for the second roller to roll along and bear against, the roller bearing plate supporting the calf panel on the second roller. When the first drive is actuated the second roller rides along the roller bearing plate toward an end thereof. When the second roller rolls off the end of the roller bearing plate, the calf panel is permitted to move downwardly relative to the main frame. The roller bearing plate further includes a ramp commencing at the end thereof, and when the second roller rolls off the end the second roller rolls along the ramp.

One advantage of the present invention is that a hospital bed is provided which includes an onboard toilet module which permits use by a patient in a conventional manner as opposed to the difficulties encountered with use of a traditional bedpan. The toilet module can be carried by the bed full-time in an onboard manner. No lengthening of the bed is required however as the toilet module fits within the footprint of a standard 93 inch long hospital bed.

Another advantage of the present invention is that a hospital bed is provided with pivoting footboard halves which are located at the foot end of the bed and which are utilizable as sideguards/handrails when a patient egresses the chair configured bed, which sideguards/handrails are repositionable prior to patent egress such that the downward load applied by the patient on the sideguards/handrails is applied intermediate the head and foot end casters thus optimizing the stability of the bed during patient egress therefrom.

Yet another advantage of the present invention is that apparatus is provided for use in conjunction with a bed which converts to a chair for stabilizing and guiding a patient from the chair configured bed to a patient care module positioned at the foot end of the bed.

Still another advantage of the present invention is that in a hospital bed which converts to a chair, bolsters are provided adjacent the lateral edges of the leg panel which, when the leg panel is dropped to form a chair, are repositionable upwardly and rearwardly to over the lateral edges of the seat panel thereby providing convenient armrests for the patient in the chair configured bed.

These and other objects and advantages of the present invention will become more readily apparent during the following detailed description taken in conjunction with the drawings herein, in which:

BRIEF DESCRIPTION OF THE DRAWINGS

FIG. 1 is a side elevational view of the hospital bed of the present invention;

FIG. 3 is the encircled area of FIG. 1 shown enlarged;

FIG. 4 is a view taken along line 4—4 of FIG. 3;

FIG. 6 is a view taken along line 6—6 of FIG. 5;

FIGS. 7A–F are views taken along line 7A—7A of FIG. 5 during downward pivoting of the leg panel;

FIGS. 9A–B are views taken along line 9A—9A of FIG. 5 during initial retraction of the patient support platform;

FIG. 10 is a view similar to FIG. 1A but with the thigh and leg panels pivoted upwardly;

DETAILED DESCRIPTION OF THE INVENTION

Figure 1A:
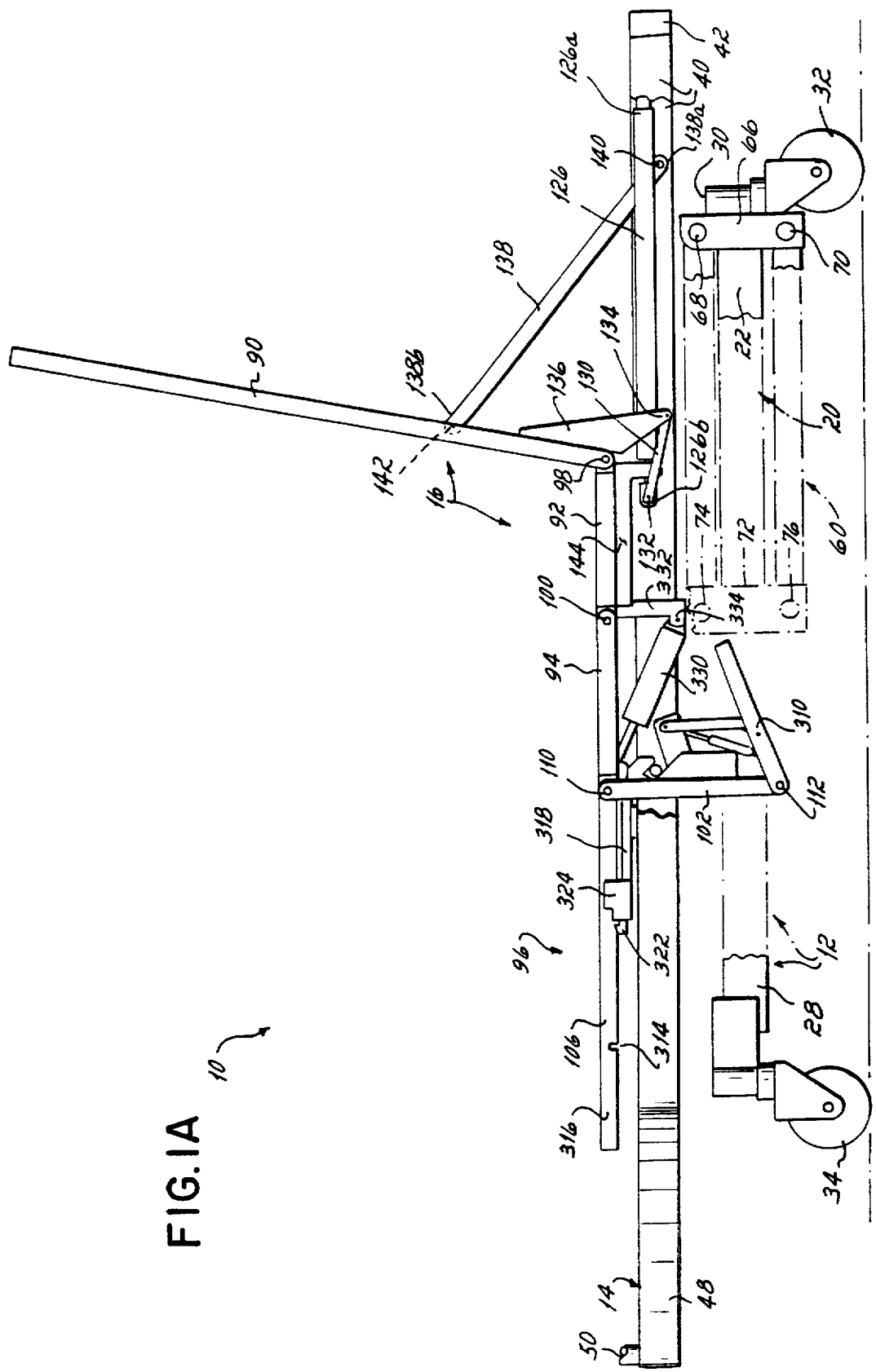
FIG. 1A is a view similar to FIG. 1 but with the patient support platform shown in a lowermost position and with the head panel pivoted upwardly and the leg panel pivoted downwardly.
Figure 2:
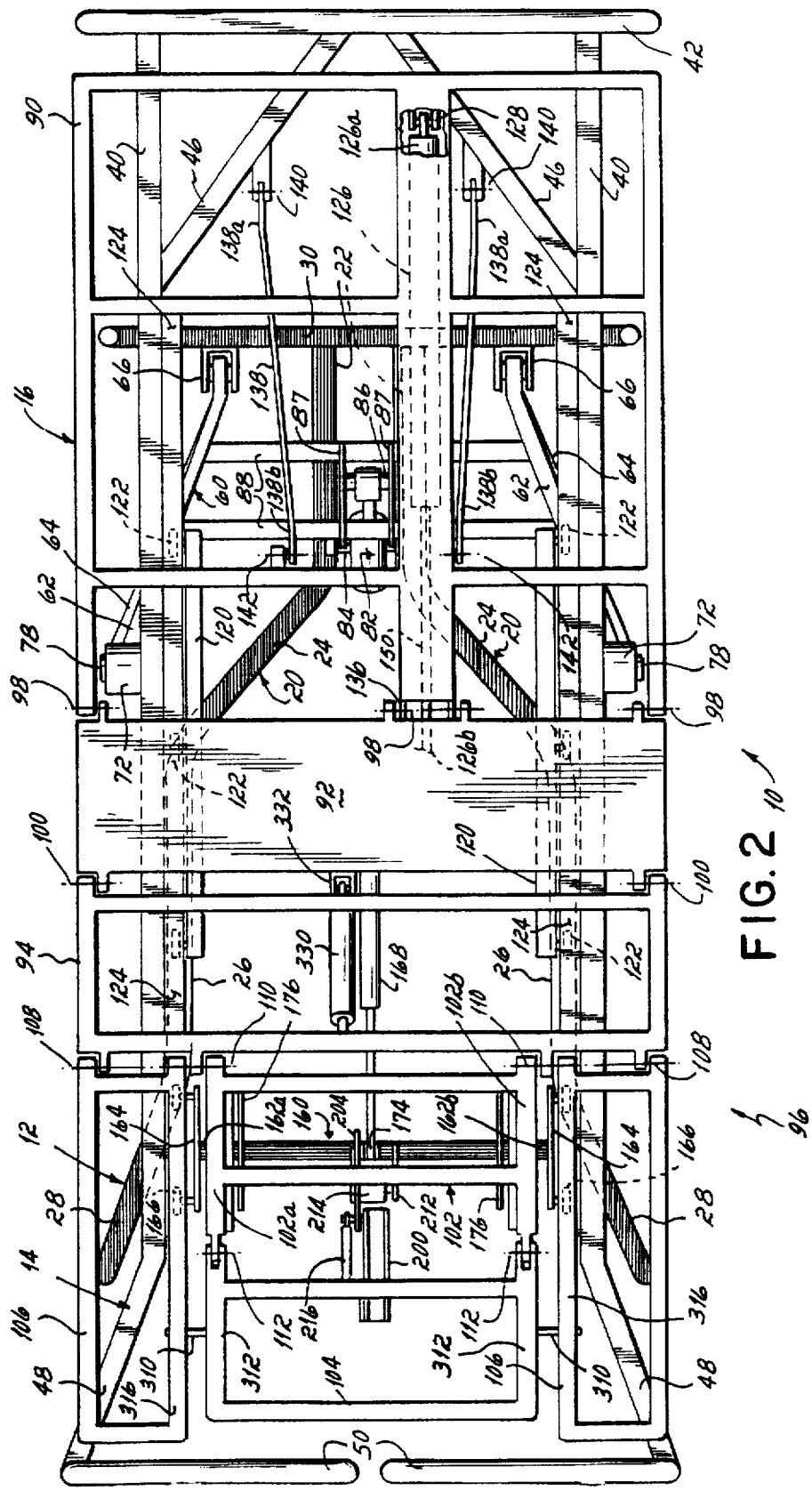
FIG. 2 is a view taken along line 2—2 of FIG. 1.
Figure 5:
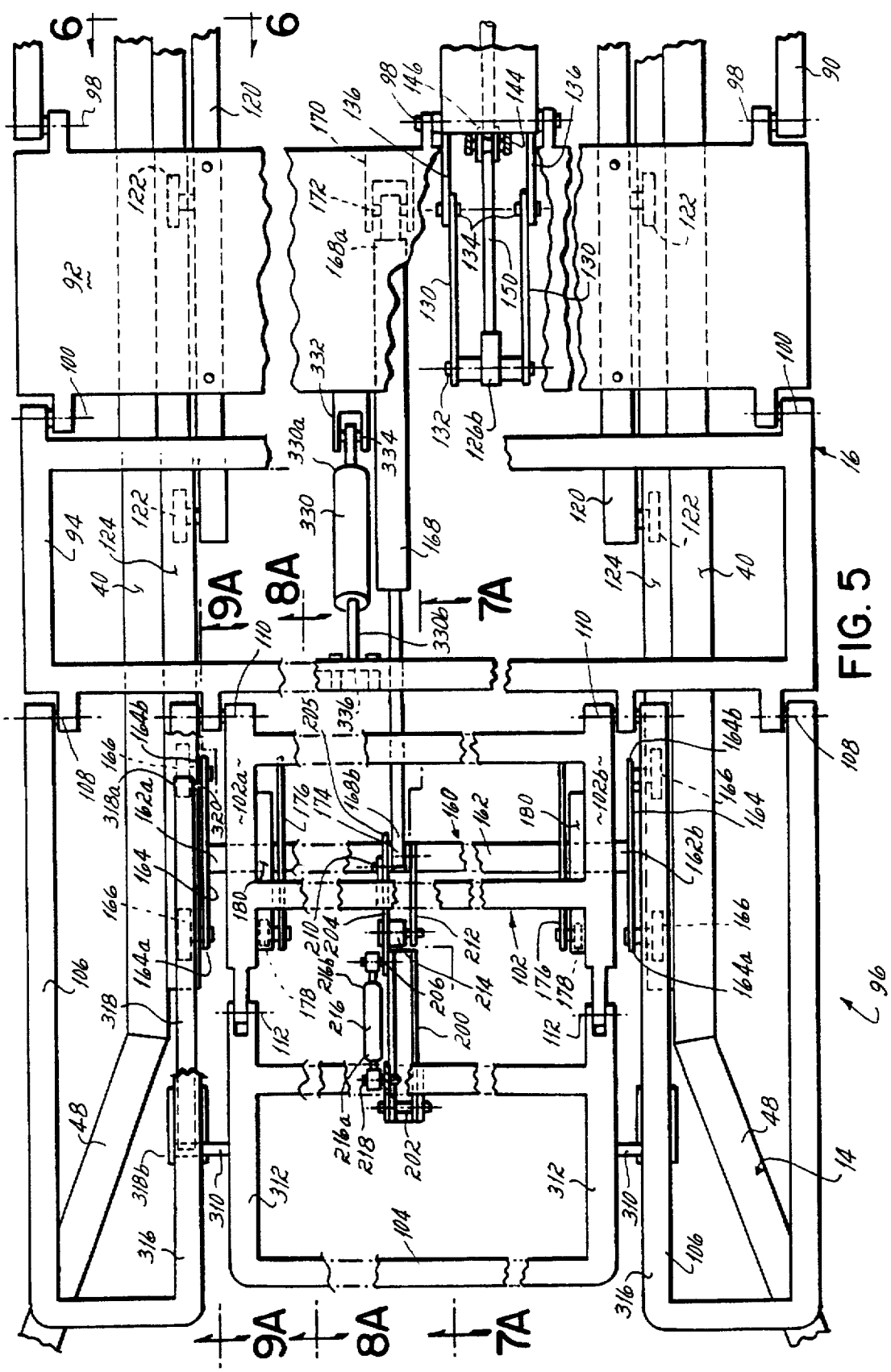
FIG. 5 is a view similar to FIG. 2 but just of the seat, thigh and leg panels.

With reference first to FIG. 1, there is illustrated a hospital bed 10 according to the present invention. The bed 10 comprises, generally, a base 12, a main frame 14 mounted above the base 12, and a patient support platform 16 movably mounted on the main frame 14.

Referring now to FIGS. 1–6, it will be seen that the base 12 of hospital bed 10 includes a pair of frame members 20, 20 each of which includes a first longitudinally oriented section 22, a first laterally outwardly diverging section 24, a second longitudinally oriented section 26 and a second laterally outwardly diverging section 28. Base 12 of hospital bed 10 is of extended length and defines a "Y" shape, the opening of which is toward the foot end of the bed 10. The advantages of the extended length and foot facing "Y" will be subsequently described.

At the head end of the base 12 there is a transverse member 30 connected to the head ends of the longitudinally oriented sections 22, 22 of the base frame members 20, 20. On the laterally outward ends of the transverse member 30 are head end casters 32. Mounted on the foot ends of sections 28, 28 of the frame members 20, 20 of the base 12 are foot end casters 34.

The main frame 14 includes a pair of longitudinally oriented rails or frame members 40 which span the length of the bed 10. Connected to the head end of each of the rails 40 is a transverse cross member 42 from which extends upwardly a headboard 44. A pair of braces 46, 46 connect the head ends of the rails 40 to the head end cross member 42. At the foot end of the main frame 14 each of the rails 40 include a laterally outwardly diverging section 48. Pivotally attached to the ends of each of the sections 48 is a pivoting footboard half 50. Pivoting footboard halves or foot gates 50, 50, when oriented transversely to the length of the bed 10, function together as a footboard. When the pivoting footboard halves 50, 50 are pivoted toward the head end of the bed 10 to a position generally parallel the length of the bed 10, the footboard halves 50, 50 function separately as sideguards/handrails for aiding a patient in egressing from the bed 10 when the bed 10 is configured as a chair. The main frame 14 is of extended or full length and has advantages which likewise will be described.

A pair of parallelogram linkages 60, 60 movably mount the main frame 14 to and above the base 12. Each parallelogram linkage 60 includes upper and lower links 62, 64 having lower ends pivotally connected to a bracket 66 mounted to member 30 of base 12 at pivots 68, 70 respectively. The links 62, 64 are pivoted at their upper ends to a bracket 72 mounted to each main frame rail 40 at pivots 74, 76. Brackets 72 are pivoted to the rails 40 at pivots 78. Main frame 14 pivots at the pivots 78, 78 relative to the linkage 60 and hence base 12 thus providing Trendelenburg and reverse Trendelenburg movement of the main frame 14 and hence the patient support platform 16. A pair of gas springs 80, 80 are located beneath rail 40 of main frame 14 and have cylinder ends connected to the lower end of each bracket 72 and piston rod ends connected to each rail 40. The two pairs of gas springs 80, 80 provide rotational resistance to the main frame 14 when positioned in the Trendelenburg and reverse Trendelenburg positions and any position in between. Gas Springs 80 may be actuated by any conventional means.

A hydraulic piston and cylinder 82 has a cylinder end pivotally connected between the sections 22 of the base frame members 20 at pivot 84 and a piston rod end pivotally connected between the upper links 62 of each parallelogram linkage 60 at a pivot connection 86. Pivot 86 is located between a pair of triangular plates 87, 87 both of which are mounted to a pair of cross braces 88, 88 spanning between and connected to upper links 62, 62 of the parallelogram linkages 60, 60. Extension and retraction of the piston and cylinder 82 moves main frame 14 upwardly and downwardly relative to the base 12.

The patient support platform 16 includes a head panel 90, a seat panel 92, a thigh panel 94 and a leg panel 96. Head panel 90 and seat panel 92 are hinged at pivot points 98, 98. Seat panel 92 and thigh panel 94 are hinged at pivot points 100, 100.

Leg panel 96 comprises a calf panel 102, a foot panel 104 and a pair of lateral side bolsters 106, 106. Lateral side bolsters 106, 106 are pivoted to thigh panel 94 at outboard pivots 108 and inboard pivots 110. Inboard pivots 110 also serve to pivot calf panel 102 to thigh panel 94. Foot panel 104 is pivoted to the calf panel 102 via pivots 112.

Seat panel 102 is mounted upon a carriage 120 which includes a pair of rollers 122, 122 on either lateral side thereof. Each pair of rollers 122, 122 rolls within an inwardly facing channel 124 secured to an inboard side of each rail 40 of the main frame 14 (FIG. 6).

A piston and cylinder 126 has a cylinder end 126a pivotally connected to the forward end of main frame 14 at pivot 128 and a piston rod end 126b pivotally connected between a pair of links 130, 130 at 132. Each of the links 130, 130 is pivotally connected at a pivot 134 to a torque plate 136 which itself is fixedly secured to the head panel 90. Extension and retraction of the piston and cylinder 126 thus serves to extend toward the foot end and retract away from the foot end the patient support platform 16 along the main frame 14, as well as to pivot downwardly and upwardly the head panel 90. Head panel 90 is additionally connected to the main frame 14 via a pair of links 138, 138 each of which has a head end 138a pivotally connected to the main frame 14 at a pivot 140 and a foot end 138b pivotally connected to the head panel 90 at a pivot 142. A bracket 144 depends from the seat panel 92 and carries an upper roller 146 and a lower roller 148. The piston rod 150 of the piston and cylinder 126 resides between the rollers 146, 148, the rollers providing support against upward and downward deflections of the rod 150. The full stroke of the piston and cylinder 126 is 18 inches. Thus, when the patient support platform 16 is in the normally horizontal and extended (retracted) attitude, rod 150 and hence pivot 132 are fully extended. Retraction of the pivot 132 18 inches toward the head end of the bed via the piston and cylinder 126 results in 12 inches of travel of the patient support platform 16 on the main frame 14 toward the head end of the bed 10, with 6 inches of motion being lost between pivots 132 and 134. Six inches of relative travel between the pivots 132 and 134 results in the head panel 90 being pivoted to the full up position via the torque plates 136, 136 (FIG. 1A); likewise, 12 inches of travel of the pivot 134 and hence pivot 98 results in the links 138, 138 driving the head panel 90 to the full up position (also FIG. 1A). The combination of torque plates 136, 136 in conjunction with links 138, 138 provides for efficient upward pivoting of the head panel 90, as torque plates 136, 136 are most effective during initial upward pivoting of head panel 90 whereas links 138, 138 are most efficient during final upward pivoting of the head panel 90.

Referring now to FIGS. 5 and 8A-F, a second carriage 160 is provided for actuation of the leg panel 96. Carriage 160 comprises a transverse member 162 and a longitudinal plate member 164 mounted on each lateral end 162a, 162b of the transverse member 162. One roller 166 of a pair of rollers 166, 166 is mounted on each end 164a, 164b of each of the longitudinal members 164, 164. Each of the two roller pairs 166, 166 rolls within one of the channels 124, 124 secured to each of the rail members 40, 40 of the main frame 14. A piston and cylinder 168 has a cylinder end 168a pivotally connected to a bracket 170 at 172, which bracket 170 is secured to the underneath side of the seat panel 92. The piston rod end 168b of the cylinder 168 is pivotally secured to the cross member 162 at 174. A plate 176 is fixedly secured to the cross member 162 inboard of each plate 164. Each plate 176 carries a roller 178. Each roller 178 rides along and in contact with a roller bearing surface or plate 180, which itself is a part of a vertically oriented downwardly extending plate 182 connected to each lateral edge 102a, 102b of the calf panel 102. The plate 182 further includes an upwardly angled ramp 184 commencing at a head end edge 186 of the roller bearing plate 180. Ramp 184 is actually one side of a channel 188 including an opposite side 190. Calf panel 102 is supported on rollers 178, 178 by virtue of the fact that each roller bearing plate 180 bears down upon and against one of the rollers 178. Each roller 178 is operable to roll along its respective roller bearing plate 180 as the piston and cylinder 168 extends and retracts. As each roller 178 rolls past each edge 186 of each plate 180 the calf panel 102 is permitted to pivot downwardly relative to the main frame 14, the operation of which will be described subsequently.

Referring now to FIGS. 5 and 7A-F, a first link 200 has a first end 200a pivoted to the foot panel 104 at pivot 202. A second link 204 has a first end 204c pivoted to the second end 200b of link 200 at 206, and a protuberance 208 on a second end 204b. Link 204 is pivoted to a bracket 205 mounted on the calf panel 102 at pivot 210. A plate 212 is fixedly secured to cross member 162 of the carriage 160. Pivotally mounted on the plate 212 is a roller 214. Roller 214 normally contacts the lower edge 204c of link 204 near the pivot 206 when the patient support platform 16 is in a generally horizontal attitude. Retraction of the piston and cylinder 168 causes the roller 212 to travel along the lower edge 204c of link 204 toward the protuberance 208. Further travel of the roller 214 causes the foot panel 104 to pivot downwardly relative to the calf panel 102, the operation of which will be described subsequently. A gas spring 216 has a piston rod end 216a pivotally mounted to the foot panel 104 at 218 and a cylinder end 216b pivotally mounted to the link 204 at the pivot 206. Gas spring 216 is normally under compression; that is to say, gas spring 216 has a tendency to extend itself.

Describing now the operation of the leg panel 96, and referring now specifically to FIGS. 7A-F, the patient support platform 16 begins in the normally horizontal, planar attitude. Initial retraction of the piston and cylinder 168 causes the roller 214 to ride along the underneath side 204c of the link 204. Continued retraction of the piston and cylinder 168 causes the roller 214 to contact the protuberance 208 on link 204. Further retraction of the piston cylinder 168 causes the link 204 to begin rotating counter-clockwise about pivot 210 due to the action of roller 214 on protuberance 208, and the action of the gas spring 216 upon link 204. Counterclockwise rotation of link 204 exerts a downward force on foot panel 104 via the connection therebetween by link 200.

Referring now to FIGS. 8A-F, which correspond in time sequence to FIGS. 7A-F, as the piston and cylinder 168 retracts, the carriage 160 travels toward the head end of the bed 10. Rollers 178, 178 which support the calf panel 102 as the roller bearing plates 180, 180 bear thereupon, travel toward the head end edges 186, 186 of the roller bearing plates 180, 180. As each roller 178 rolls past each edge 186, gravity allows the calf panel 102 to begin dropping downwardly by pivoting at pivot: 110 as the channels 188, 188 collapse downwardly onto the rollers 178, 178, the rollers 178, 178 rolling upwardly relative to the ramps 184, 184 each of which is one side of the channels 188, 188.

Figure 8A:
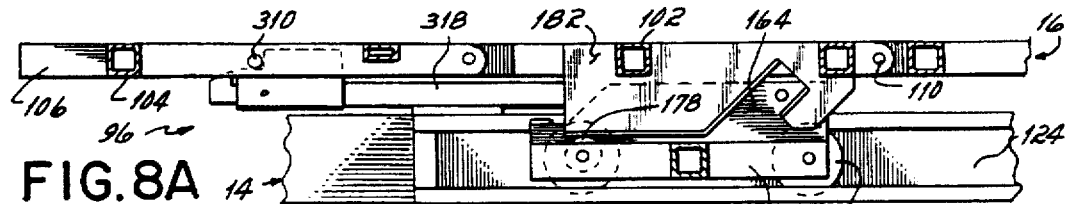
FIGS. 8A–F are views taken along line 8A—8A of FIG. 5 also during downward pivoting of the leg panel.
Figure 8B:
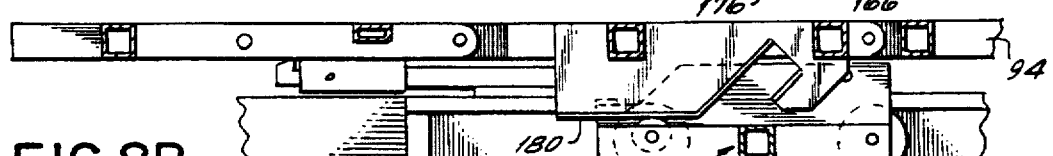
Figure 8C:
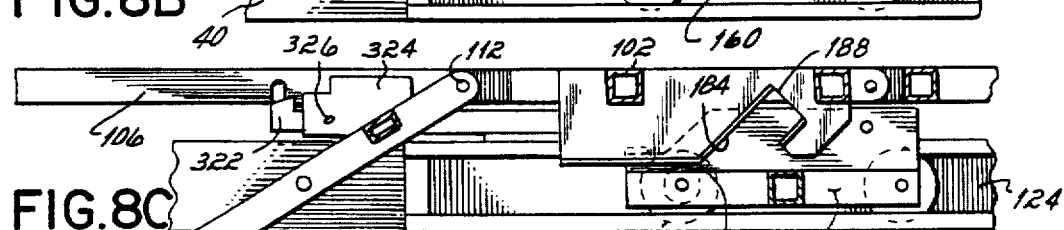
Figure 8D:
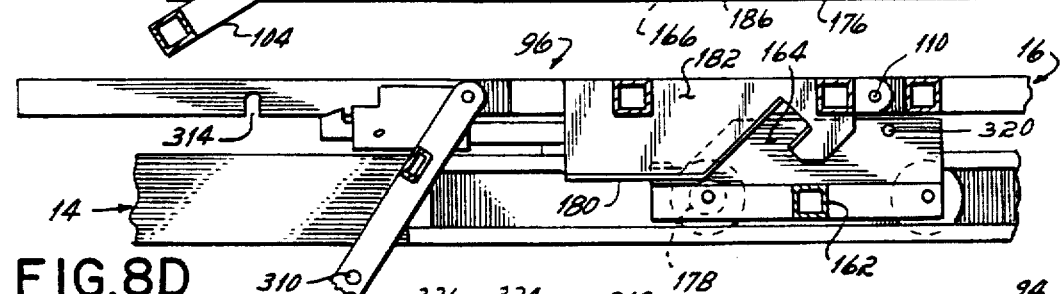
Figure 8E:
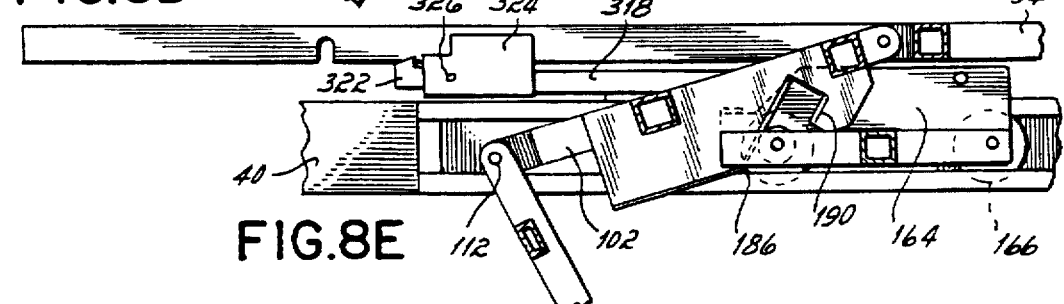
Figure 8F:
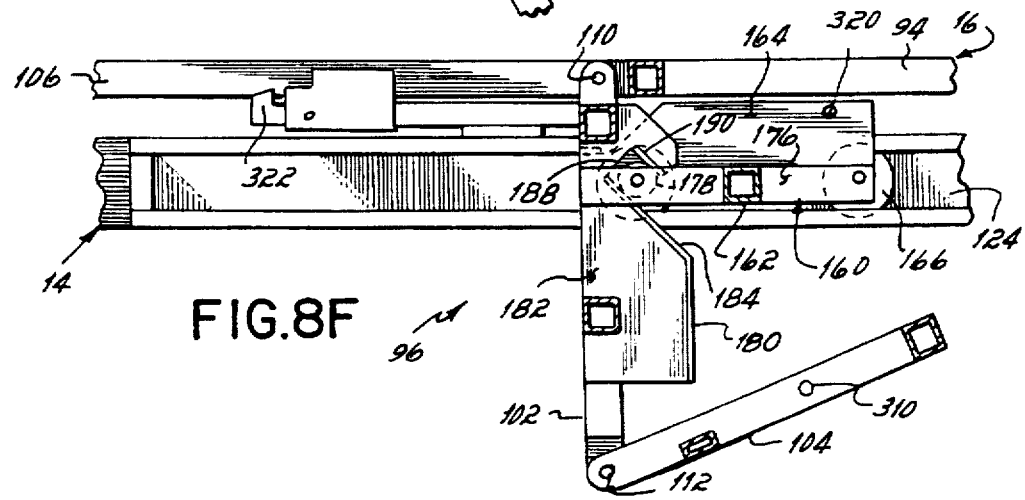

Thus, complete retraction of the cylinder 168 results in the condition shown in FIGS. 1A, 7F and 8F wherein the foot panel 104 has been pivoted relative to the calf panel 102 by slightly more than 90°, and wherein the calf panel 102 has been pivoted relative to the thigh panel 94 by approximately 90°. And, full retraction of the piston and cylinder 126 causes the patient support platform 16 to be translated toward the head end of the bed 10 and the head panel 90 to be pivoted to the upwardmost position (FIG. 1A). Thus, in this configuration, the bed 10 is configured as a chair.

Figure 13:
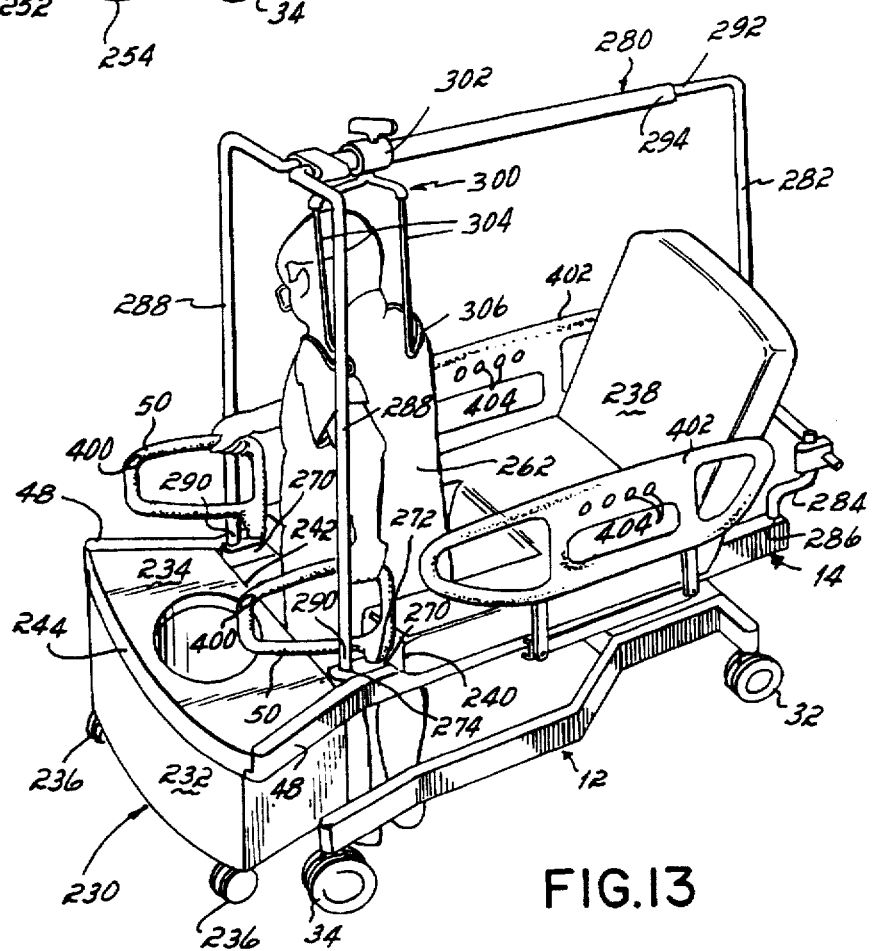
FIG. 13 is a perspective view of the hospital bed of the present invention shown in conjunction with a toilet module and a patient safety harness.

Referring now to FIG. 13, the hospital bed 10 of the present invention is shown with a toilet module 230 used in conjunction therewith. Toilet module 230 includes a toilet portion 232, a seat portion 234 and casters 236. The seat 236 can conveniently slidably engage the sections 48, 48 of the rails 40, 40 of the main frame 12. The toilet 232 may then be rolled underneath the seat 234. Alternatively, the assembled seat 234 and toilet 232 may remain attached to the main frame 40, and carried with the bed 10 as an onboard toilet module. Toilet module 230 conveniently fits within the footprint of the standard 92 inch length hospital bed 10, thus requiring no lengthening of bed 10, and is normally concealed by the leg panel 96. In use of the hospital bed 10 with the toilet module 230, the bed would be in its normally horizontal attitude with the leg section 96 concealing the module 30 and the patient 262 lying supine upon the mattress 238 atop the patient support platform 16. A preferable mattress for use with the hospital bed 10 of the present invention is disclosed in application Ser. No. 08/234,403. Piston and cylinder 126 is then energized to translate the entire patient support platform 16 towards the head end of the bed 10 relative to the main frame 14. Head panel 90 pivots upwardly during this retraction as described above. Once the patient support platform 16 has been fully retracted atop the main frame 14 as detected by appropriate sensors known to those skilled in the art, appropriate control circuitry and the like, likewise known to those skilled in the art, energizes piston and cylinder 168. Since the patient support surface 16 has been fully retracted prior to activation of downward pivoting of the foot and calf panels 104 and 102 respectively, the foot end edge 240 of foot panel 104 has cleared the head end edge 242 of the toilet module 230, the dimension of the toilet module 230 from head end edge 242 to foot end edge 244 being slightly less than the 12 inches of horizontal travel traversed by the patient support 16 on the main frame 14. Pivoting of the foot panel 104 relative to the calf panel 102 and pivoting of the calf panel 102 relative to the thigh panel 94 then proceeds as discussed above in connection with the discussion of FIGS. 7A-F and FIGS. 8A-F, respectively. As described in applications Ser. Nos. 08/234,403 and 08/186,657, the patient support platform 16 is lowerable to a lowermost position to allow a patient's feet to rest directly on the floor. Bed controls, known to those skilled in the art, may be located on the foot gates 50, 50 as illustrated at 400, on the standard sideguards 402 as illustrated at 404, or both to allow for manipulation of the bed 10.

Once the patient's feet are securely placed on the floor, the patient can employ the vertical lift piston and cylinder 82, activated by patient controls 400 or 404 on the foot gates 50, 50 or sideguards 402, respectively, to power lift the patient to an upright position, as described in applications Ser. Nos. 08/234,403 and 08/186,657. Once in the upright standing position, the patient can turn 180° so as to be seated upon seat 234, which has traveled upwardly with main frame 14 during the above-described vertical lift assist. Since the seat 234 is in a high position, the transition from standing to sitting is eased for the patient. The main frame 14 and toilet module seat 234 can then be lowered to a comfortable sitting position for the patient. Once patient elimination is complete, the vertical lift cylinder 82 can be activated by the patient utilizing the patient controls 400 or 404 to urge the patient to a standing position, at which time the patient can turn back 180° so as to be in a position to again sit in the chair configured bed. The bed can then be lowered to ease the patient back into the sitting position. See FIGS. 19A-D.

Figure 12:
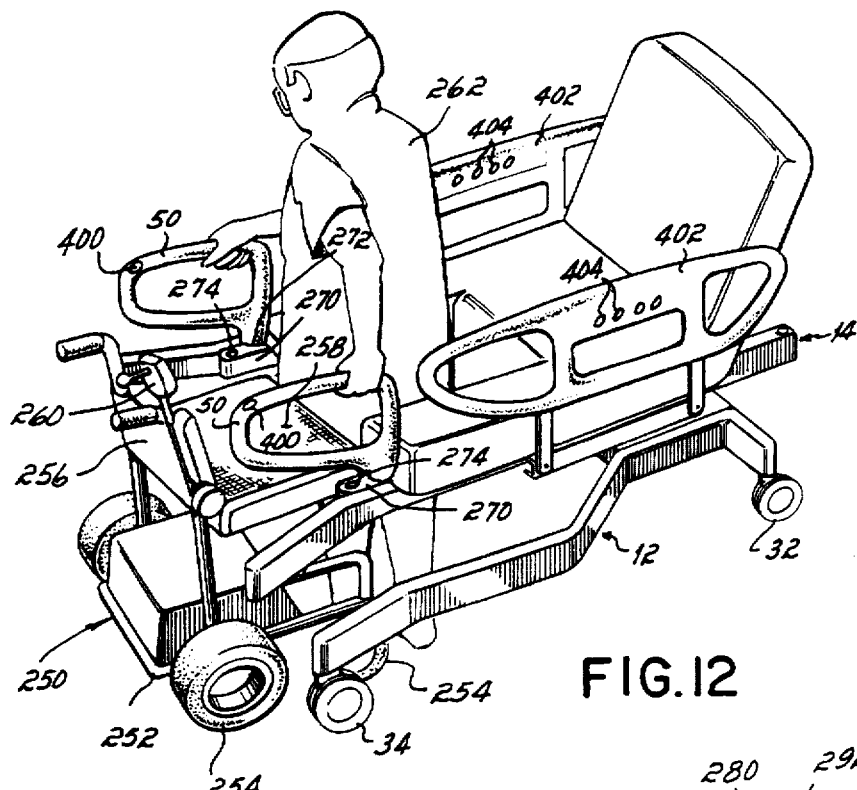
FIG. 12 is a perspective of the hospital bed of the present invention shown in conjunction with a wheelchair.

Similarly, the hospital bed 10 of the present invention can be used in conjunction with other patient care modules, such as, for example, the wheelchair module 250 as shown in FIG. 12. Such a wheelchair 250 would include a base 252, wheels 254, a backrest 256, a seat 258 and appropriate controls 260. As with the toilet module 230, the wheelchair module 250 could be docked to the bed 10 as an onboard module which travels with the bed 10. The seat 258 would, as with the toilet module 230, reside under and normally be concealed by the leg section 96 and would travel upwardly and downwardly with main frame 14 to assist a patient in sitting on and rising from the wheelchair 250. As with the toilet module 230, the leg section 96 would retract from over the seat 258 at which time downward pivoting of the foot and calf portions 104 and 102 respectively would occur thus providing access to the wheelchair module 252 by a patient 262.

Figure 11:
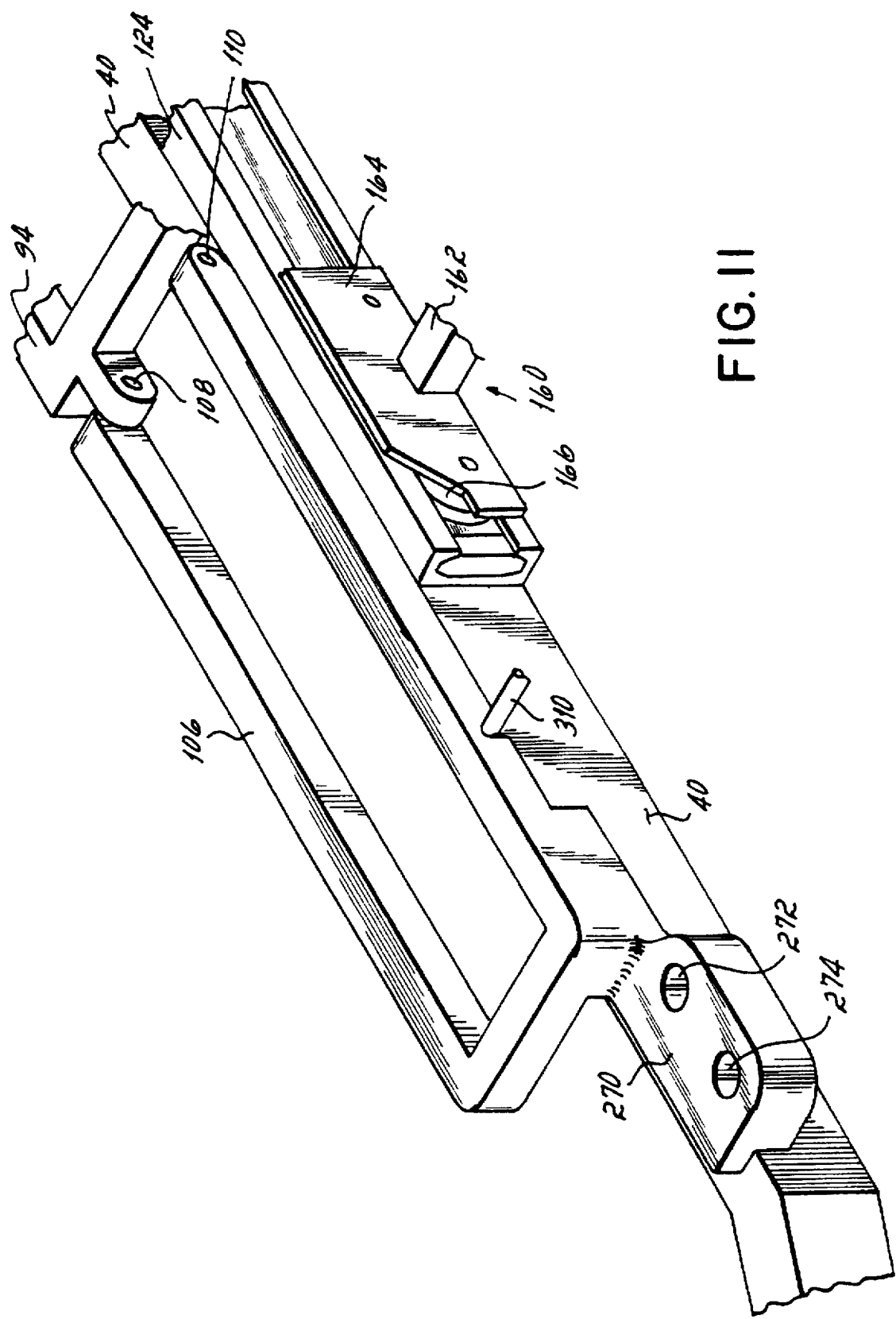
FIG. 11 is a perspective view of a bolster and associated orthopedic frame and foot gate sockets.

An alternative form of mounting for the pivoting footboard halves or foot gates 50, 50 and which allows for those footboard halves 50, 50 to be repositioned such that any weight applied thereon by a patient, such as shown in FIGS. 12 and 13, would be applied between or intermediate of the head end casters 32 and foot end casters 34 of the bed 10 is shown in FIG. 11. In FIG. 11, an extension 270 is secured to each bolster 106. Each extension 270 would include a foot gate socket 272 and a fracture frame socket 274 (the use of which will be described subsequently). Thus, rather than being pivotally mounted to the ends of the sections 48,48 of the rails 40, 40 of the main frame 14, the pivoting footboard halves 50, 50 would be pivotally mounted within the foot gate sockets 272, 272 as by a shaft (not shown) depending from the bottom of each footboard half or foot gate 50. Thus, as the patient support platform 16 retracts atop the main frame 14 by virtue of the action of the piston and cylinder 126, the footboard halves 50, 50 travel with the patient support platform 16 .such that they are repositioned to a position intermediate the head end casters 32 and foot end casters 34. Thus, when swung from their positions generally transverse to the bed 10 at which they function together as a footboard, to their positions generally parallel the longitudinal dimension of the bed 10, the footboard halves 50, 50 may function as sideguards/handrails as shown in FIGS. 12 and 13 thus aiding a patient 262 in moving from the chair configured bed 10 to a patient care module such as the toilet module 230 or wheelchair module 250. The downward force applied by the patient 262 to the sideguards/handrails 50, 50 is thus directed within the footprint of the casters, thus providing for optimum bed stability when egressing the bed and alighting upon one of the patient care modules.

As shown in FIG. 13, a frame 280 is provided for use with the hospital bed 10. The frame 280 includes a vertical head end portion 282 which includes appropriate lower ends, one of which is shown at 284, for insertion into sockets 286 in the head ends of each of the rails 40, 40 of the main frame 14. The frame 280 further includes vertical foot end portions 288, 288 having appropriate lower ends 290, 290 for insertion into the fracture frame sockets 274, 274. To accommodate the changes in relative distance between the foot end vertical members 288 and the head end vertical member 282 a pair of telescoping horizontal members 292 and 294 are provided such that the frame 280 can extend and retract as the patient support platform 16 extends and retracts. The frame 280 can be used as a fracture or orthopedic frame. In that case, the frame and traction apparatus associated therewith remain in the same relative position to a patient 262 supported on the bed 10 during extension and retraction of the patient support platform 16.

In addition, the frame 280 can include a safety harness 300 which is operable to travel the length of the frame 280. Harness 300 includes a traveling collar 302 slidably mounted on frame member 294. Vertical tethers 304, 304 connect the collar 302 to a vest 306 worn by the patient 262. The traveling harness 300 helps to provide security and stability to the patient 262 as the patient egresses from the bed 10 configured as a chair and moves from a sitting position to a standing position and onto a patient care module positioned at the foot end of the bed 10.

Referring now to FIGS. 5, 9A–B and 10, a pin 310 is fixedly secured to each lateral rail 312 of the foot section 104. Pin 310 normally resides in a slot 314 in the underneath side of inboard lateral rail 316 of the bolster 106. A link 318 has a first end 318a pivoted to plate 164 of carriage 160 at 320. The second end 318b of the link 318 includes an upturned finger portion 322 thereon. A block 324 is pivoted to link 318 at pivot 326. Block 324 includes a notch 328 in an upper forward corner thereof including a horizontal surface 328a and a vertical surface 328b.

A piston and cylinder 330 includes a cylinder end 330a pivotally connected to an L-shaped bracket 332 connected to seat panel 92 at pivot 334. A piston rod end 330b is pivotally connected to the thigh panel 94 at a pivot 336. Piston and cylinder 330 is operable to pivot thigh panel 94 and the entire leg panel 96 upwardly to provide for elevation of a patient's feet and legs.

For piston and cylinder 330 to raise the entire leg section 96 upwardly to the position shown in FIG. 10, piston and cylinder 330 is energized prior to any retraction of the patient support platform 15. As pivots 108, 110 move upwardly due to the action of the piston and cylinder 330, pin 310 acting upon vertical surface 328b of block 324 causes block 324 and hence the link 318 to pivot upwardly about pivot 320. Thus, the foot panel 104 and the bolsters 106 which are connected thereto via the pins 108, 310 remain in a generally horizontal attitude as the thigh panel 94 is pivoted upwardly. As can be seen in FIG. 10, when the leg panel 96 is in the raised position, the hook portion 322 of the link 318 hooks over the pin 310. Thus, the leg panel 96 comprising the calf panel 102, foot panel 104 and side bolsters 106, 106 remains locked against any inadvertent further upward lifting which could tend to disengage the leg panel 96 from the links 318, 318 and blocks 324, 324.

As is best seen and understood in FIGS. 7A–B and 9A–B, during initial retraction of carriage 160 via piston and cylinder 168, the horizontal surface 328a of the block 324 is moved from under the pin 310, and the hook portion 322 of link 318 is moved to the head end side of the pin 310. Since pin 310 is thus free to drop out of the groove 314, foot panel 104 is thus freed to pivot downwardly relative to the side bolsters 106, 106.

Figure 15:
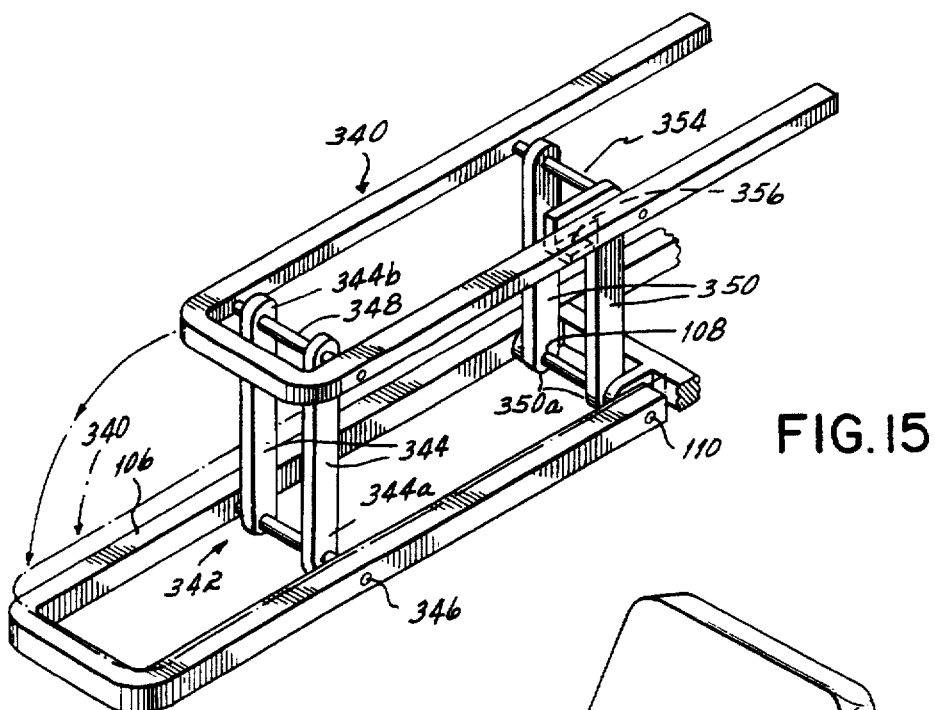
FIG. 15 is a perspective view of an alternative form of bolster.

Referring now to FIG. 15, there is shown an alternative form of the bolster 106. In this form, bolster 106 includes an additional or upper bolster frame member 340 pivotally connected to the standard lower bolster 106 via a parallelogram linkage 342. Parallelogram linkage 342 includes a first pair of links 344, 344 each of which is pivotally connected on a first end 344a to a pivot 346, and each of which includes a second end 344b pivoted to the frame member 340 at pivot 348. A second pair of links 350, 350 each has a first end 350a pivoted to bolster 106 at pivots, 108, 110 and a second end 350b pivoted to the frame member 340 at pivot 354. One of the links 350 includes a stop 356 and associated latch mechanism (not shown) which is brought into contact with the lower surface of the frame 340 thus limiting further pivoting movement of the frame member 340 and securing it in the elevated rearward position.

Figure 15A:
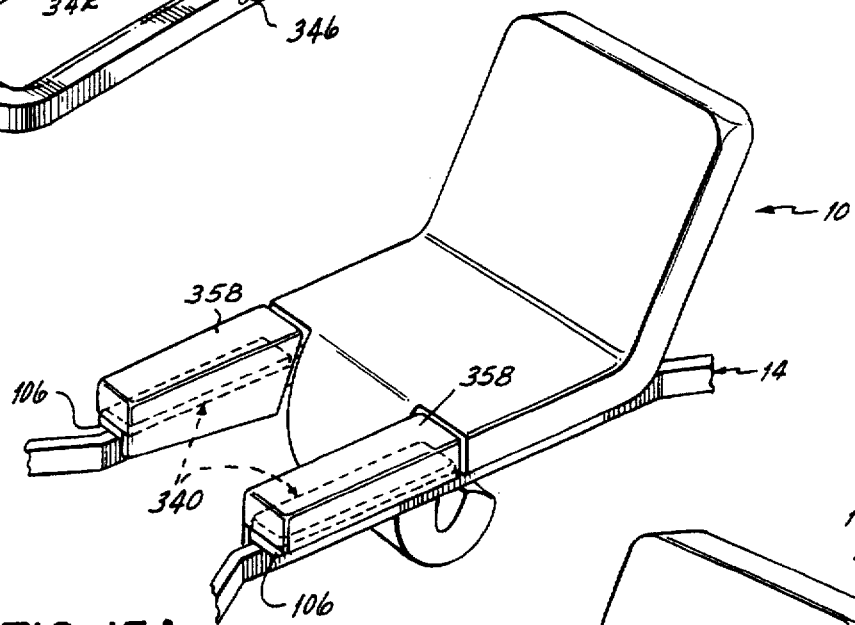
FIGS. 15A–B are perspective views of a hospital bed incorporating the bolsters of FIG. 15.
Figure 15B:
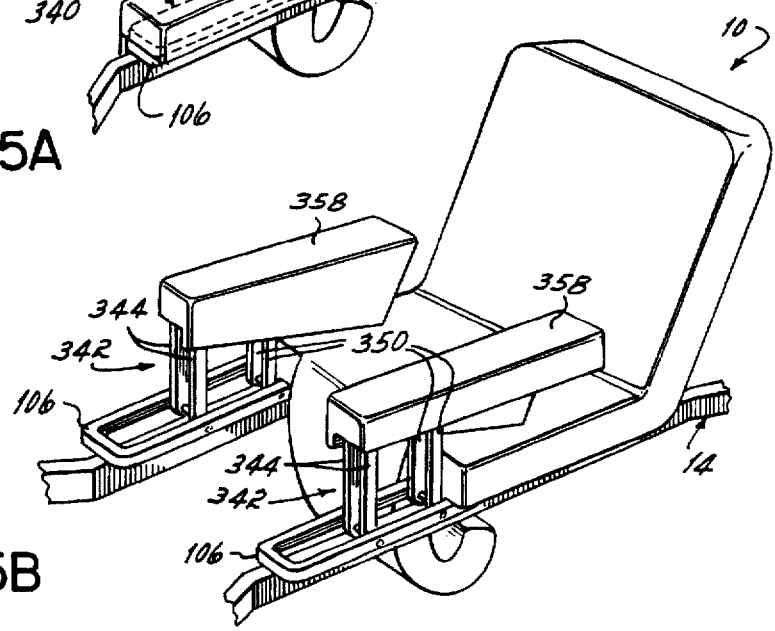

FIGS. 15A and 15B show the alternative form of the bolsters 106, 106 including pivoting bolster/arm rest portions 340. In these Figures, the frame members 340 are covered with suitable padding and fabric 358. When each of the frame members 340 is in a position juxtaposed to the bolsters 106, the combination bolster 106 with upholstered frame member 340 serves as a side-to-side protective restraint for a patient similar to the prior bolster embodiment. When the bed 10 is configured in a chair position, as shown in FIGS. 15A and 15B, the upholstered frame members 340 may be pivoted from a low forward position to a high rearward position; that is the upholstered frame members 340 are movable from a position forward of and in a plane defined by the seat panel 92 to a position above and along each lateral edge of the seat panel 92 when the leg panel 96 is pivoted downwardly and the head panel 90 is pivoted upwardly, thus providing convenient armrests for a patient situated atop the bed 10 configured as a chair.

Figure 14:
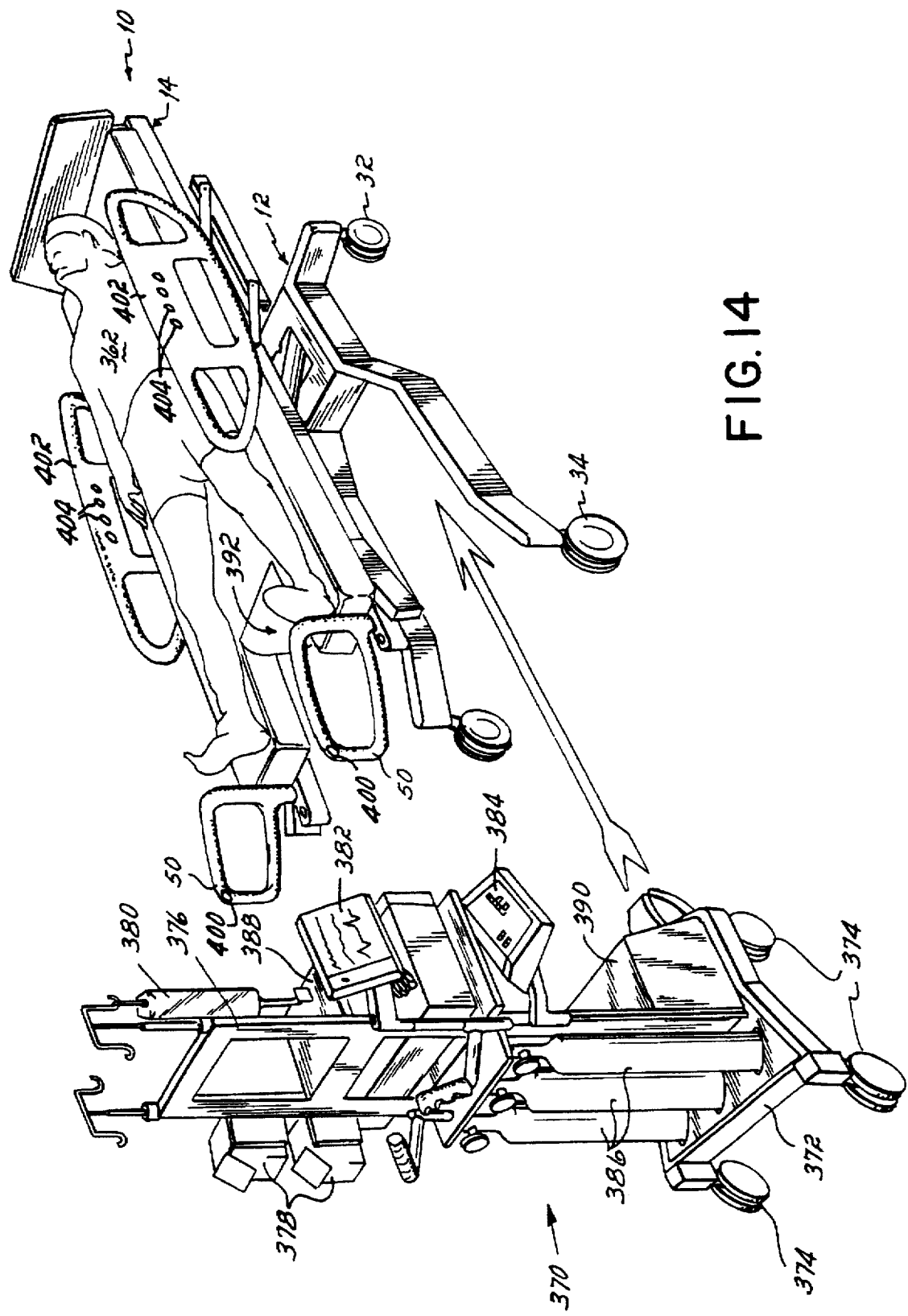
FIG. 14 is a perspective view of the hospital bed of the present invention shown in conjunction with a mobile power column.

Referring now to FIG. 14, the bed 10 is shown in conjunction with a mobile power column 370. Mobile power column 370 includes a base 372, casters 374 mounted to the base 372, and an upright support 376 connected to the base 372. The upright support 376 may support infusion pumps 378 and infusion solution bags 380, a monitor 382, a keyboard 384, air and/or oxygen tanks 386 and a ventilator 388. A housing 390 mounted to base 372 may house batteries (not shown) and the like, as well as a motorized drive (not shown) for powering the mobile power column 370. With a patient 262 situated atop the bed 10, and with the leg panel 96 folded downwardly, a convenient cavity 392 is formed in the foot end of the bed 10 which may be taken advantage of for docking the mobile power column 370 to the bed 10 for mobile transport of the patient 362 and critical care apparatus with the entire combination taking up no more space than the bed 10 alone.

Figure 16:
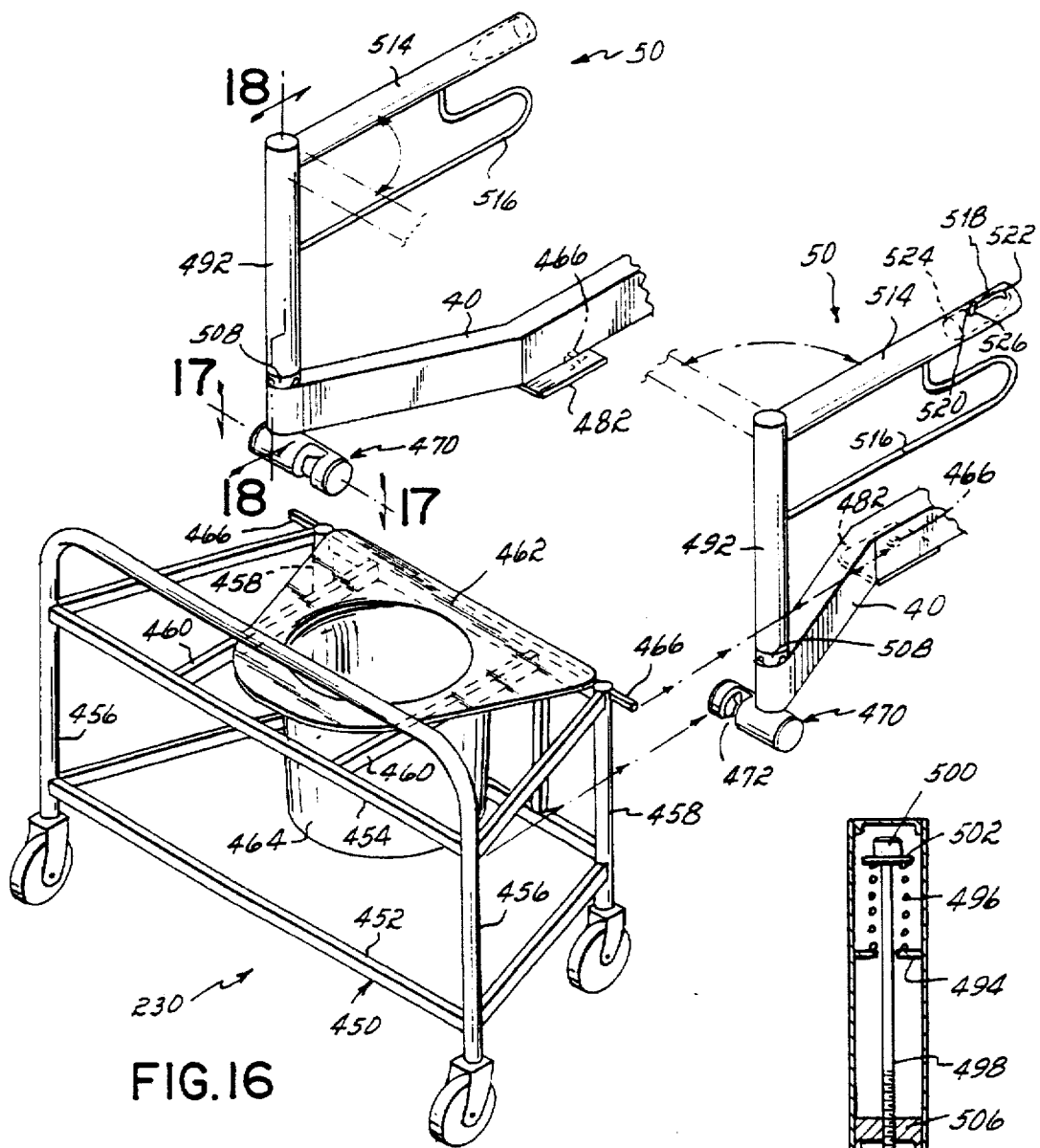
FIG. 16 is a perspective view of the foot end of the main frame with preferred embodiments of the toilet module, toilet module latches and foot gates.
Figure 17:
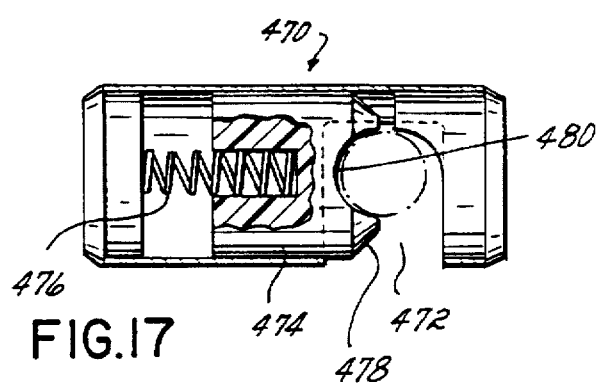
FIG. 17 is a view taken along line 17—17 of FIG. 16.
Figure 18:
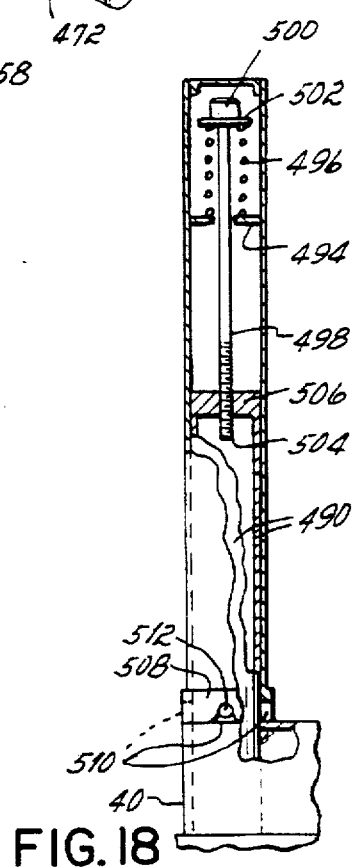
FIG. 18 is a view taken along line 18—18 of FIG. 16.
Figures 19A, 19B:
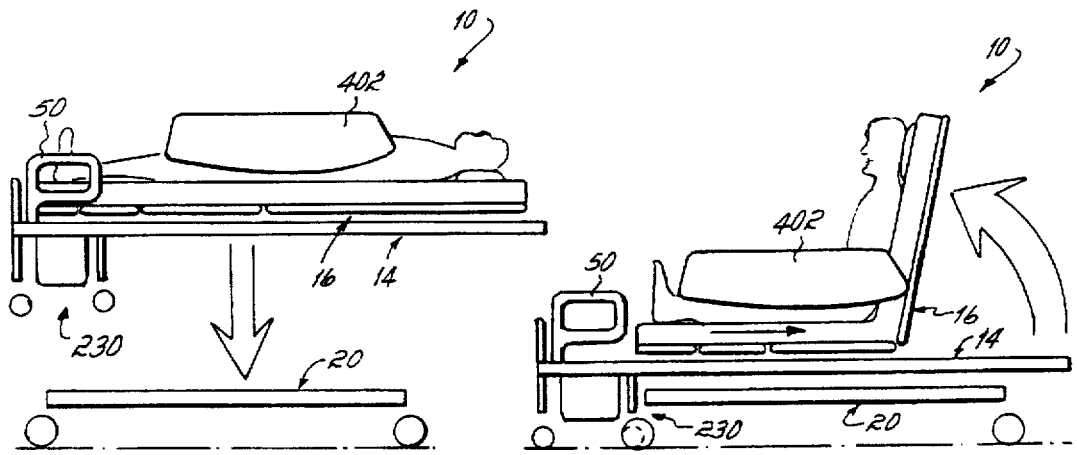
FIGS. 19A–E are sequence side elevation views of the bed of the present invention.
Figures 19C, 19D:
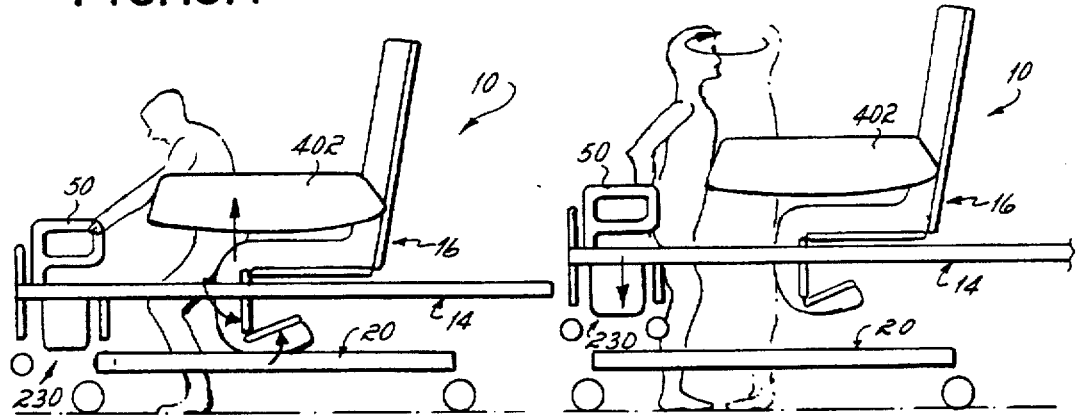
Figure 19E:
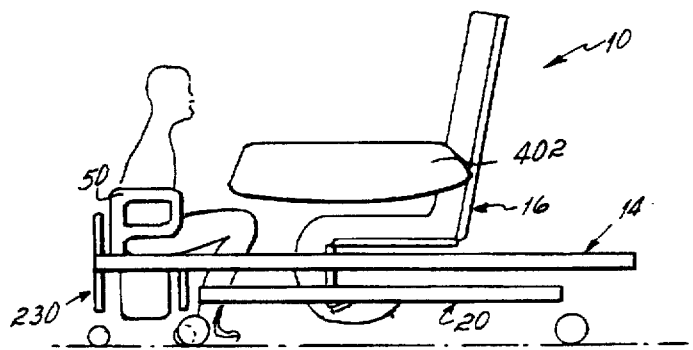

Referring now to FIGS. 16–18, and with like numbers referring to like elements, preferred embodiments of the toilet module 230 and foot gates 50, 50 are illustrated. Toilet module 230 comprises a framework 450 including a lower trapezoidal frame 452, an upper trapezoidal frame 454 and upwardly extending rear vertical posts 456, 456 and upwardly extending forward vertical posts 458, 458. A pair of longitudinal struts 460, 460 span the upper rectangular frame 454 and support a toilet seat 462 from which depends a toilet chamber 464. A laterally extending bar 466 extends laterally outwardly from the upper end of each forward post 458, the use for which will be subsequently described.

A latch block 470 is secured to the lower end of each of the rails 40. Each latch block 470 takes the form of a tube and includes a notch 472 therein for accepting a respective vertical support 456. A plunger 474 is spring loaded towards a closed position via a compression spring 476 within the latch block 470. The plunger 470 includes a chamfer 478 and a semicircular groove 480 therein. Chamfer 478 aids in compressing the latch block 474 and hence compression spring 476 by support 456. Once the vertical pole 456 reaches the semicircular notch 480 the plunger 474 snaps securely against the pole 456.

An ear of a pair of ears 482, 482 is secured to the lowermost side of each of the rails 40, 40 of the main frame 14. When the toilet module 230 engages the main frame 14, the laterally extending bars 466 are supported by the ears 482. Once the module 230 is docked to the main frame 14, module 230 may travel upwardly and downwardly with the main frame 14 as it is raised and lowered, the bars 466 being supported by the ears 482, and the rear corners of the upper frame 454 being supported by the latch blocks 470.

A preferred form of foot gate 50 includes an inner tube 490 welded to the rail 40 at the foot end thereof. An outer tube 492 slidably resides over the inner tube 490. Outer tube 492 includes a washer 494 welded therein, the upper surface of which supports a compression spring 496. A screw 498 has a head 500 which exerts a downward force on a washer 502 and hence spring 496, the lower end 504 of which is threaded into the upper end 506 of the inner tube 490. The lower end of the outer tube 492 includes an exterior collar 508 which includes four equally spaced notches 510 therein. Notches 510 accept a pin 512 pressed into the lower end of the inner tube 490. Thus, outer tube 492 is spring biased downwardly relative to inner tube 490. An upper tube 514 is fixedly secured to the upper end of the outer tube 492. A lower support rail 516 is connected to the tube 514 and the outer tube 492. One of the tubes 514 includes a U-shaped groove 518 therein including notches 520 and 522. A plug 524 includes a pin 526 which engages the groove 518. When the tubes 514 are rotated to a position wherein they are collinear, pin 526 may be moved from notch 520 to notch 522 thus causing the plug 524 to move into engagement with the end of the other tube 514 thereby locking the foot gates together. When unlocked, horizontal force applied to the ends of the tubes 514 cause the notches 510 to ride upwardly and over the pins 512 until the next notch is reached at which time the outer tube 494 snaps downwardly back over the pin 512.

It will therefore be appreciated that the hospital bed of the present invention provides a number of distinct advantages. The Y-shaped bed base, opening toward the foot end, provides a cavity into which a patient care module may reside, such as toilet module or wheelchair, and which also provides room for a patient to maneuver to sit upon that module. No lengthening of a standard hospital bed is required to accommodate the patient care module. The extended length base allows the foot gates to be repositionable intermediate the head end and foot end castors and to serve as hand rails as the patient sits upon the patient care module. Apparatus is provided for guidingly assisting a patient onto a patient care module. Bolsters include armrests which are pivotable upwardly and toward a head end of the bed for patient comfort and security when sitting in the chair configured bed. The full length main frame allows for patient care modules to be connected to a foot end thereof.

Those skilled in the art will readily recognize numerous adaptations and modifications which can be made to the present invention which will result in an improved hospital bed, all of which will fall within the spirit and scope of the present invention as defined in the following claims. Accordingly, the invention is to be limited only by the scope of the following claims and their equivalents.

What is claimed is:

1. A hospital bed comprising:
   a base with casters;
   a main frame mounted above said base;
   a patient support platform longitudinally movably mounted on said main frame and including head and leg panels;
   means for moving said patient support platform longitudinally toward a head end of said main frame; and
   means for pivoting said leg panel downwardly after said patient support platform has a traveled a predetermined distance toward said head end of said main frame.

2. The hospital bed of claim 1 wherein said bed includes a patient care module disposed beneath said patient support platform and normally concealed by said leg panel, and wherein said means for moving said patient support platform causes said leg panel to retract from over said patient care module to expose said patient care module for use, at which time said means for pivoting said foot panel downwardly allows a patient supported in said bed to move from said patient support platform to the floor and then to said patient care module.

3. The hospital bed of claim 2 wherein said patient support platform further includes a pair of bolsters one of which is disposed on either lateral side of said leg panel, said bolsters spanning between said head panel and patient care module to provide side support to the patient when moving from said patient support platform to the patient care module and back.

4. The hospital bed of claim 1 further including means for moving said head panel upwardly as said means for moving said patient support platform moves said platform longitudinally toward a head end of said main frame.

5. The hospital bed of claim 1 wherein said leg panel comprises a calf panel pivoted relative to said main frame and a foot panel pivoted to said calf panel.

6. The hospital bed of claim 5 wherein said means for pivoting said foot panel includes:
   means for pivoting said foot panel downwardly relative to said calf panel; and
   means for pivoting said calf panel downwardly relative to said main frame.

7. A hospital bed comprising:
   a base with casters;
   a main frame mounted above said base;
   a patient support platform longitudinally movably mounted on said main frame and including head and leg panels pivotally moveable relative to said main frame;
   a first drive for moving said patient support platform longitudinally toward a head end of said bed; and
   a second drive for pivoting said leg panel downwardly after said patient support platform has traveled a predetermined distance toward said head end of said main frame.

8. The hospital bed of claim 7 wherein said leg panel comprises:
   a calf panel pivoted relative to said main frame; and
   a foot panel pivoted to said calf panel.

9. The hospital bed of claim 8 further including:
   a first linkage operable between said foot and calf panels for pivoting said foot panel relative to said calf panel; and
   a second linkage operable between said calf panel and main frame for pivoting said calf panel relative to said main frame;
   both said linkages being actuated by said second drive.

10. The hospital bed of claim 9 wherein said first linkage comprises:

a first link having first and second ends, said first end being pivoted to said foot panel;

a second link having first and second ends, said first end being pivoted to said second end of said first link, said second end having a protuberance thereon, said second link being pivoted to said calf panel intermediate said first and second ends; and a roller operably connected to said first drive and normally contacting said second link intermediate said first and second ends;

whereby when said first drive is actuated said roller rides along said second link towards said protuberance, said second link rotating in response thereto and causing a force to be applied to said first link which moves said foot panel downwardly relative to said calf panel.

11. The hospital bed of claim 10 wherein said first linkage further includes a spring operable between said foot panel and said first end of said second link to aid in rotating said second link.

12. The hospital bed of claim 9 wherein said second linkage comprises:

at least a second roller operably connected to said first drive;

said calf panel including a roller bearing plate for said second roller to roll along and bear against, said roller bearing plate supporting said calf panel on said second roller;

whereby when said first drive is actuated said second roller rides along said roller bearing plate toward an end thereof, and when said second roller rolls off said end, said calf panel is permitted to move downwardly relative to said main frame.

13. The hospital bed of claim 12 wherein said roller bearing plate further includes a ramp commencing at said end thereof, and when said second roller rolls of said end said second roller rolls along said ramp.

* * * * *